United States Patent
Ishikawa et al.

(10) Patent No.: US 7,419,973 B2
(45) Date of Patent: *Sep. 2, 2008

(54) PHOSPHONOCEPHEM COMPOUND

(75) Inventors: Tomoyasu Ishikawa, Shiga (JP); Shohei Hashiguchi, Osaka (JP); Yuji Iizawa, Kyoto (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 280 days.

This patent is subject to a terminal disclaimer.

(21) Appl. No.: 11/063,715

(22) Filed: Feb. 23, 2005

(65) Prior Publication Data

US 2005/0176697 A1 Aug. 11, 2005

Related U.S. Application Data

(63) Continuation of application No. 10/343,285, filed as application No. PCT/JP01/06904 on Aug. 10, 2001, now Pat. No. 6,906,055.

(30) Foreign Application Priority Data

Aug. 10, 2000 (JP) ............................. 2000-247966
Nov. 21, 2000 (JP) ............................. 2000-354959

(51) Int. Cl.
*A61K 31/546* (2006.01)
*A61P 31/04* (2006.01)
*C07F 9/6561* (2006.01)

(52) U.S. Cl. .................................................... 514/203
(58) Field of Classification Search ................... None
See application file for complete search history.

(56) References Cited

U.S. PATENT DOCUMENTS 5,948,774 A * 9/1999 Kamiyama et al. .......... 514/203
6,417,175 B1 7/2002 Ishikawa et al.
6,906,055 B2 * 6/2005 Ishikawa et al. ............ 514/203

FOREIGN PATENT DOCUMENTS

EP 1 043 327 A1 10/2000
JP A-9-100283 4/1997
WO WO 99/32497 1/1999

OTHER PUBLICATIONS

Tomoyasu Ishikawa, Bioorganic & Medicinal Chemistry, vol. 11, Issue 11, May 29, 2003, pp. 2427-2437.*
"Acetonitrile" <http://www.lakes-environmental.com/toxic/ACETONITRILE.HTML> downloaded from the internet Jul. 30, 2004.*
Ishikawa, T. et al., "TAK-599, a Novel N-Phosphono Type Prodrug of Anti-MRSA Cephalosporin T-91825: Synthesis, Physicochemical and Pharmacological Properties" *Bioorganic & Medicinal Chemistry* (2003), vol. 11, pp. 2427-2437.
"Acetonitrile" [Factsheet] <http://www.lakes-environmental.com/toxic/ACETONITRILE.HTML>.
Giron et al., "Thermal analysis and Calorimetric Methods in the Characterisation of Polymorphs and Solvates", *Thermochimica Acta*, Elsevier Science Publishers, Amsterdam, NL, vol. 248, 1995, pp. 1-59.

* cited by examiner

*Primary Examiner*—Mark L Berch
(74) *Attorney, Agent, or Firm*—Edwards Angell Palmer & Dodge LLP; David G. Conlin; Gregory B. Butler, Esq.

(57) ABSTRACT

A cephem compound (particularly its crystal) represented by the formula [I], wherein X is $CH_3COOH$, $CH_3CH_2COOH$ or $CH_3CN$, and n is 0 to 5, is useful as an antibacterial agent (particularly anti-MRSA agent) and shows superior quality such as high solid stability, possible long-term stable preservation and the like.

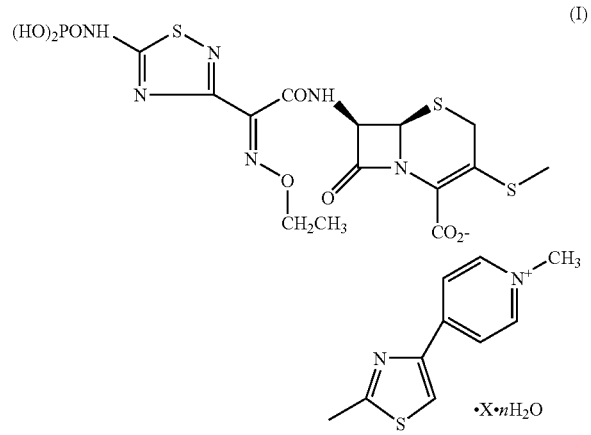

23 Claims, 5 Drawing Sheets

PHOSPHONOCEPHEM COMPOUND

This application is a continuation of U.S. patent application Ser. No. 10/343,285 filed Jan. 29, 2003 now U.S. Pat. No. 6,906,055, issued Jun. 14, 2005, which was the National Phase filing of International Patent Application No. PCT/JP01/06904, filed Aug. 10, 2001.

TECHNICAL FIELD

The present invention relates to a compound (particularly a crystal thereof) useful as a pharmaceutical agent of a phosphonocephem compound having a superior antibacterial activity and a production method thereof.

BACKGROUND ART

JP-A-11-255772 discloses phosphonocephem compounds having a superior antibacterial activity, wherein a lyophilized product of 7β-[2(Z)-ethoxyimino-2-(5-phosphonoamino-1,2,4-thiadiazol-3-yl)acetamido]-3-[4-(1-methyl-4-pyridinio)-2-thiazolylthio]-3-cephem-4-carboxylate represented by the formula:

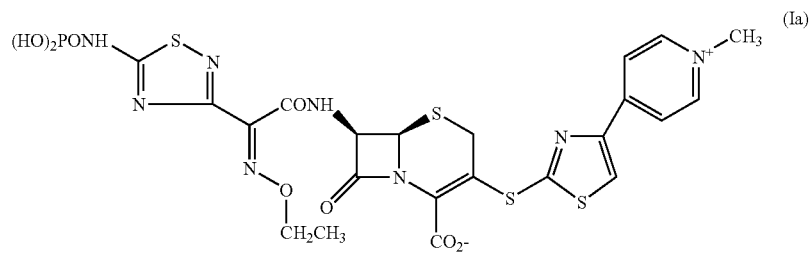

is described as one of the specific examples thereof.

In general, pharmaceutical agents are desired to be superior in quality such as absorbability, solubility, purity, stability, preservability, tractability and the like. Thus, the problem of the present invention is to provide an antibacterial agent (particularly anti-MRSA agent) having such quality as sufficiently satisfactory as a pharmaceutical product.

DISCLOSURE OF THE INVENTION

The present inventors have intensively conducted various studies in view of the above-mentioned problem, selected, from among a number of phosphonocephem compounds, a phosphonocephem compound having a particular chemical structure represented by the above-mentioned formula (Ia) and found that, when this compound, water and a particular solvent ($CH_3COOH$, $CH_3CH_2COOH$ or $CH_3CN$) are mixed and dissolved, a compound (particularly a crystal obtained by successful crystallization) having an antibacterial activity, which is particularly superior in quality as a pharmaceutical product, can be obtained unexpectedly, and that this compound has more than sufficient superior quality as a pharmaceutical product (e.g., having high solid stability and high purity, and the like), which resulted in the completion of the present invention.

Accordingly, the present invention relates to (1) a compound of the formula:

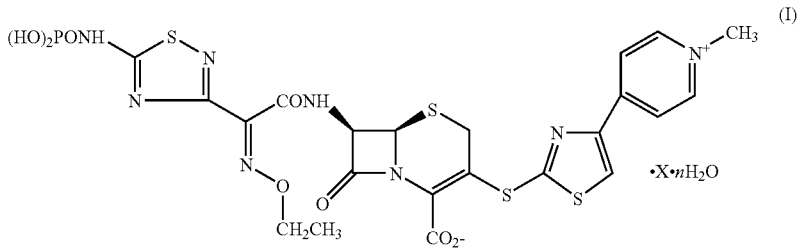

wherein X is $CH_3COOH$, $CH_3CH_2COOH$ or $CH_3CN$, and n is 0 to 5, (2) the compound of the above-mentioned (1), which is in the form of a crystal, (3) the compound of the above-mentioned (1), wherein n is 1, (4) the compound of the above-mentioned (1) or (2), wherein X is $CH_3COOH$, (5) the compound of the above-mentioned (4), having peaks near diffraction angles of 16.32, 19.06, 19.90, 20.98 and 23.24° in powder X-ray diffraction, (6) the compound of the above-mentioned (4), having peaks near diffraction angles of 11.82, 17.16, 17.80, 19.32, 20.00, 21.20, 21.78, 22.94, 24.10 and 27.02° in powder X-ray diffraction, (7) the compound of the above-mentioned (1) or (2), wherein X is $CH_3CH_2COOH$, (8) the compound of the above-mentioned (7), having peaks near diffraction angles of 16.30, 18.84, 19.70, 21.80 and 23.18° in powder X-ray diffraction, (9) a pharmaceutical composition, comprising the compound of the above-mentioned (1) or (2),

(10) the pharmaceutical composition of the above-mentioned (9), which is an antibacterial agent,

(11) a production method of a crystal of a compound represented by the formula:

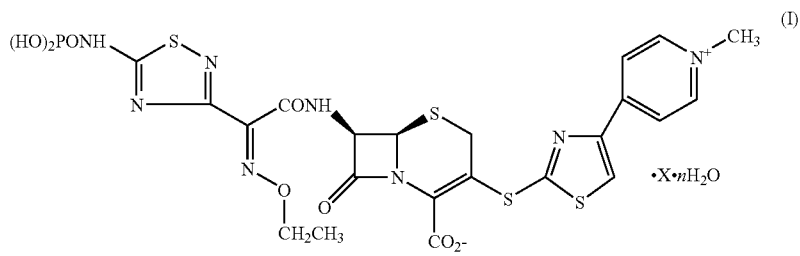

wherein X is $CH_3COOH$, $CH_3CH_2COOH$ or $CH_3CN$, and n is 0 to 5, which comprises mixing [i] a compound represented by the formula:

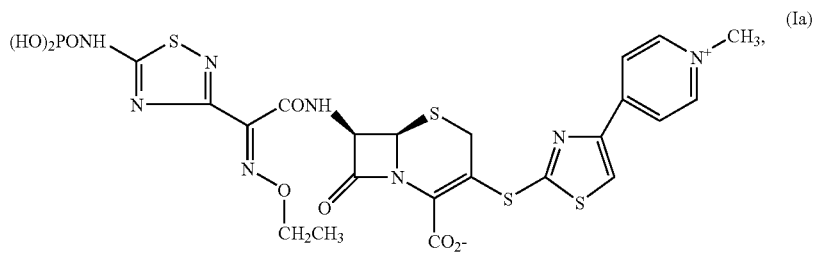

[ii] $CH_3COOH$, $CH_3CH_2COOH$ or $CH_3CN$ and [iii] water, dissolving them and allowing crystallization to take place,

(12) the production method of the above-mentioned (11), wherein the proportion (volume ratio) to be used of $CH_3COOH$, $CH_3CH_2COOH$ or $CH_3CN$:water is 1:0.1-10,

(13) a crystal obtained by mixing [i] a compound represented by the formula:

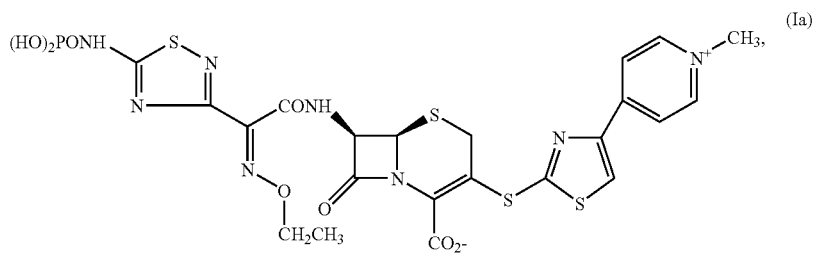

[ii] $CH_3COOH$, $CH_3CH_2COOH$ or $CH_3CN$ and [iii] water, dissolving them, and allowing crystallization to take place,

(14) a disodium salt of a compound represented by the formula:

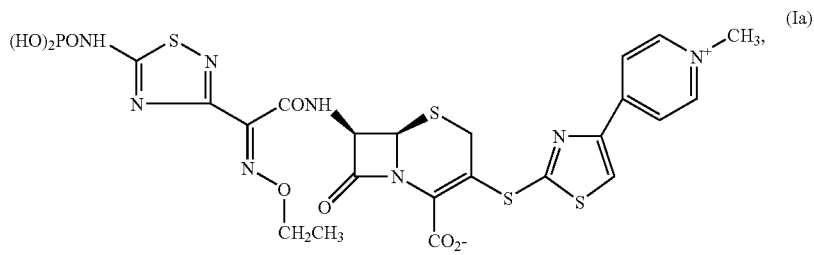

(15) the disodium salt of the above-mentioned (14), which is in the form of a crystal,
(16) the disodium salt of the above-mentioned (14) or (15), having a peak near a diffraction angle of 17.02, 18.94, 22.86, 23.36 or 26.48° in powder X-ray diffraction, and the like.

DETAILED DESCRIPTION OF THE INVENTION

Figure 1:
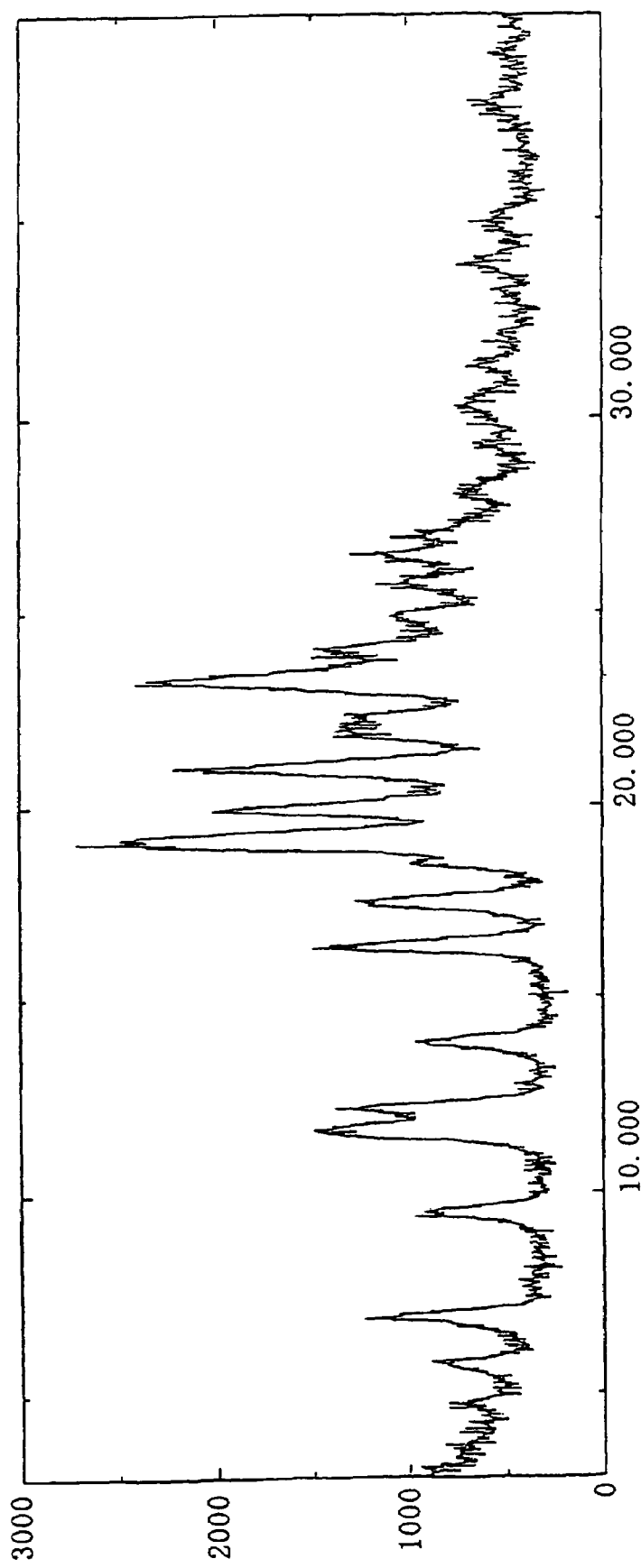
FIG. 1 shows a powder X-ray diffraction spectrum (Cu, 40 kV, 50 mA) of the compound obtained in Example 1, wherein the transverse axis shows a diffraction angle (2θ) and the vertical axis shows a peak intensity.

The compound (I) consists of 1 molecule of compound (Ia), 1 molecule of acetic acid, propionic acid or acetonitrile, and 0 to 5 molecules of water. The compound (I) may be a salt formed by compound (Ia) and acetic acid or propionic acid, or a solvate formed by compound (Ia) and acetic acid, propionic acid or acetonitrile. The compound (I) may contain water, in which case water may be incorporated as crystal water or simply adhering water. The compound (I) preferably takes the form of a crystal in view of purity and solid stability.

The compound (I) can be produced from [i] compound (Ia), [ii] acetic acid, propionic acid or acetonitrile and [iii] water. As the compound (Ia), a lyophilized product described in JP-A-11-255772 may be used, or compound (Ia) obtained by adding, for example, hydrochloric acid, sulfuric acid, nitric acid and the like to a solution containing a disodium salt, dipotassium salt or diammonium salt of compound (Ia). The solution containing the above-mentioned disodium salt of compound (Ia) may be a reaction mixture containing a disodium salt of compound (Ia), which is obtained as a result of various reactions for synthesizing a disodium salt of compound (Ia), or may be one wherein a crystal of disodium salt of compound (Ia) is dissolved. The compound (I) can be produced by mixing the above-mentioned [i], [ii] and [iii] to give a solution, and isolating from this solution by a general isolation technique such as crystallization and the like. The order of mixing [i], [ii] and [iii] is arbitrary. For example, [i] and [ii] are first mixed and the mixture may be mixed with [iii], or [i] and [iii] are mixed and the mixture may be mixed with [ii], or [ii] and [iii] are mixed and the mixture may be mixed with [i]. To give a solution after mixing, for example, ultrasonication (ultrasonic irradiation), stirring and the like are preferably applied. Upon making a solution, crystals may be simultaneously produced. When crystallization does not occur, crystallization may be caused by, for example, cooling, giving stimulation such as ultrasonication, stirring and the like, adding a seed crystal, and the like. To control physical property of the precipitated crystals, crystallization may be caused after adding saccharides to the mixture.

The mixing ratio of solvent [ii] and water [iii] for crystallization in a volume ratio of [ii]:[iii] is generally 1:0.1-10, preferably 1:0.5-5, particularly preferably about 1:1. The amounts of [ii] and [iii] to be used relative to [i] for crystallization are not particularly limited as long as they are within the range that allows for crystallization. The total amount of [ii] and [iii] relative to 1 part by weight of [i] is generally 2-100 parts by weight, preferably 3-50 parts by weight, still preferably 5-30 parts by weight. The crystallization can be conducted by a crystallization technique such as cooling the above-mentioned solution, reducing the amounts of [ii] and [iii] in vacuo, adding a seed crystal and the like. The saccharides can be added to the mixed solution in an amount up to the maximum amount that can be dissolved in [iii]. It is added relative to [i] generally in 0.05-10 parts by weight, preferably 0.1-0.5 part by weight. Generally, saccharide is preferably dissolved in [iii] for use. Examples of the saccharide include glucose, mannitol, sucrose, sorbitol, xylitol, fructose, maltose and the like, particularly preferably glucose and mannitol.

The compound (I) thus obtained can be separated from the solution by a general separation technique (e.g., filtration, centrifugation and the like) and purified by a general purification technique (e.g., washing with solvent and the like).

Because the thus-obtained compound (I) (particularly its crystal) has, for example, high purity and is superior in solid stability and the like, it can be used as a pharmaceutical preparation.

The crystal of compound (I) can have different water content according to the degree of drying. One free of water is encompassed in the scope of the present invention.

The compound (Ia) can be converted to a dialkali salt such as disodium salt, dipotassium salt, diammonium salt and the like. The dialkaline salt of compound (Ia) can be produced by, for example, adding, for example, sodium hydroxide, sodium carbonate, sodium acetate, sodium hydrogencarbonate, potassium hydroxide, potassium carbonate, potassium acetate, potassium bicarbonate, aqueous ammonia, ammonium carbonate, ammonium acetate and the like to alkalify a solution containing compound (Ia) [e.g., a reaction solution containing compound (Ia) immediately after production (when hydrophilic solvent is not contained, it is added), a solution of compound (Ia) dissolved in hydrophilic solvent, and the like]. The hydrophilic solvent is, for example, organic acids such as acetic acid, propionic acid, lactic acid, succinic acid and the like, nitrites such as acetonitrile and the like, ketones such as acetone and the like, alcohols such as methanol, ethanol and the like, ethers such as dioxane, tetrahydrofuran and the like, and the like, and hydrophilic organic solvent such as mixed solvents thereof and the like, and a mixed solvent thereof with water. Of these, acetic acid, propionic acid, acetonitrile, methanol, ethanol, lactic acid and a mixed solvent thereof with water are preferable, particularly, acetonitrile, methanol, ethanol, acetic acid, propionic acid, and a mixed solvent thereof with water are preferable.

The crystal of disodium salt of compound (Ia) can be produced by, for example, crystallization of disodium salt of compound (Ia) from the above-mentioned hydrophilic solvent.

When crystallization is conducted, the amount of disodium salt of compound (Ia) and the solvent to be used is not particularly limited as long as crystallization can take place. It is generally 2-100 parts by weight, preferably 3-50 parts by weight, still preferably 5-30 parts by weight, of the solvent per part by weight of the disodium salt. The crystallization can be conducted by a crystallization technique such as cooling the above-mentioned solution, reducing the amounts of solvent and water in vacuo, adding a seed crystal and the like.

The crystal obtained by such crystallization is separated from the solution by a general separation technique (e.g., filtration, centrifugation and the like) and can be purified by a general purification technique (e.g., washing with solvent and the like).

Because the thus-obtained crystal of disodium salt of compound (Ia) has high purity, it can be used for producing compound (Ia) and the like. For example, when producing compound (Ia), the compound (Ia) is once crystallized as its disodium salt, the crystal is separated and dissolved in the aforementioned hydrophilic solvent, to which hydrochloric acid, sulfuric acid, nitric acid or the like is added to convert the compound to compound (Ia), whereby compound (Ia) can be obtained at high purity and in high yield.

Since the compound (I) has a superior antibacterial activity and a broad-spectrum antibacterial activity and shows low toxicity, it can be used safely for the prophylaxis or treatment of various diseases in various mammals (e.g., mouse, rat, rabbit, dog, cat, cattle, pig and the like) including human, which are caused by pathogenic bacteria, such as sinopulmonary infection and urinary tract infection. The bacteria to be the target when compound (I) is used as an antibacterial agent are not particularly limited as long as compound (I) shows an antibacterial activity thereon, and a wide range of gram-positive bacteria and gram-negative bacteria can be the target. The compound (I) particularly shows a superior antibacterial activity against staphylococcus and methicillin-resistant staphylococcus aureus (MRSA). It is considered that the compound (I) is converted to a compound represented by the formula:

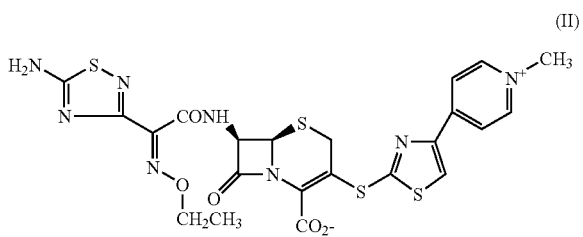

(II)

[hereinafter referred to simply as compound (II)] in biological organisms and shows an antibacterial activity.

The compound (I) (particularly its crystal) shows superior stability and can be parenterally or orally administered as injection, capsule, tablet or granule, like known penicillin preparations and cephalosporin preparations, and is preferably administered particularly as an injection. When it is administered as an injection, the dose thereof as compound (I) is, for example, generally 0.5-80 mg/day, more preferably 2-40 mg/day, per 1 kg of the body weight of a human or animal infected with the aforementioned pathogenic bacteria, and is generally administered in 2 or 3 times a day in divided doses.

When it is used as an injection, the crystal of compound (I) and a solvent (e.g., distilled water, physiological saline, 5% glucose solution and the like) are generally packaged separately to provide an injection, and the crystal of compound (I) is dissolved in a solvent when in use for administration. It is also possible to administer compound (I) after mixing with a medical infusion solution such as clinical nutrition and the like. It is preferable that the injection generally contain a pH adjuster, examples of which include carbonate, phosphate, acetate and citrate of alkaline metal or alkaline earth metal (e.g., carbonates such as sodium carbonate, potassium carbonate, sodium hydrogencarbonate, potassium bicarbonate, calcium carbonate and the like, phosphates such as trisodium phosphate, sodium dihydrogen phosphate, disodium hydrogen phosphate, dipotassium hydrogen phosphate, potassium dihydrogen phosphate, calcium hydrogen phosphate, calcium dihydrogen phosphate and the like, acetates such as sodium acetate, potassium acetate, calcium acetate and the like, citrates such as disodium citrate, sodium citrate, sodium dihydrogen citrate, calcium citrate and the like), basic amino acids (e.g., L-arginine, L-lysin and the like), N-methylglucamine and the like, and of these, an injection containing carbonate of alkaline metal or alkaline earth metal and a basic amino acid is preferable. L-Arginine is particularly preferable. Such pH adjusters are used in an amount that makes the pH of the injection solution when in use 4 to 10, preferably 4.5 to 8.5, more preferably 5.0 to 8.0, still preferably 5.0 to 7.5. When L-arginine is used, it is used in an amount of generally 0.1 equivalent-5.0 equivalents, preferably 2.0-3.5 equivalents, more preferably 2.5-3.2 equivalents, relative to the active component. These pH adjusters are generally packaged in a state in which they are dissolved in a solvent. However, they may be mixed with the crystal of compound (I) and packaged, or may be packaged separately from the crystal of compound (I) and the solvent, and mixed when in use. Moreover, the stability of an injection solution when in use can be enhanced by adding solubilizing agents having reductability to the above-mentioned injection. Examples of the solubilizing agents having reductability include sodium sulfite, sodium hydrosulfite, sodium hydrogen sulfite, sodium pyrosulfite, L-cysteine and the like. These reducing agents are used in an-amount of generally 0.001 equivalent-2.0 equivalents, preferably 0.01-0.5 equivalent, more preferably 0.05-0.2 equivalent, relative to the active component. These solubilizing agents having reductability are generally packaged in a state in which they are divided in a solvent. However, they may be mixed with the crystal of compound (I), may be mixed with a pH adjuster, or may be packaged separately from the crystal of compound (I), the pH adjuster and the solvent and mixed when in use.

The content of the crystal of compound (I) in an injection preparation, calculated as compound (Ia), is 100-2000 mg, preferably 200-1000 mg.

The proportion of a solvent in an injection preparation in weight ratio is 10-500, preferably 20-300, relative to the crystal of compound (I) as 1. The proportion of a pH adjuster is generally 1.0-3.0 equivalents of pH adjuster relative to 1 equivalent of the crystal of compound (I), calculated as compound (Ia).

The pharmaceutical composition of the present invention may contain only compound (I), or may contain a carrier generally used for pharmaceutical agents (e.g., solvent and the above-mentioned pH adjuster in the case of injection) and the like.

Of the compounds (I), a compound wherein X is $CH_3COOH$ or $CH_3CH_2COOH$ and a crystal thereof are preferable. When X is $CH_3COOH$, a compound having peaks near diffraction angles of 16.32, 19.06, 19.90, 20.98 and 23.24° in powder X-ray diffraction, and a compound having peaks near diffraction angles of 11.82, 17.16, 17.80, 19.32, 20.00, 21.20, 21.78, 22.94, 24.10 and 27.02° in powder X-ray diffraction are particularly preferable. When X is $CH_3CH_2COOH$, a compound having peaks near diffraction angles of 16.30, 18.84, 19.70, 21.80 and 23.18° in powder X-ray diffraction is particularly preferable. The "near" in the above-mentioned diffraction angle means ±0.2°.

Now the production methods of compound (Ia) used as a starting material in the present invention are described.
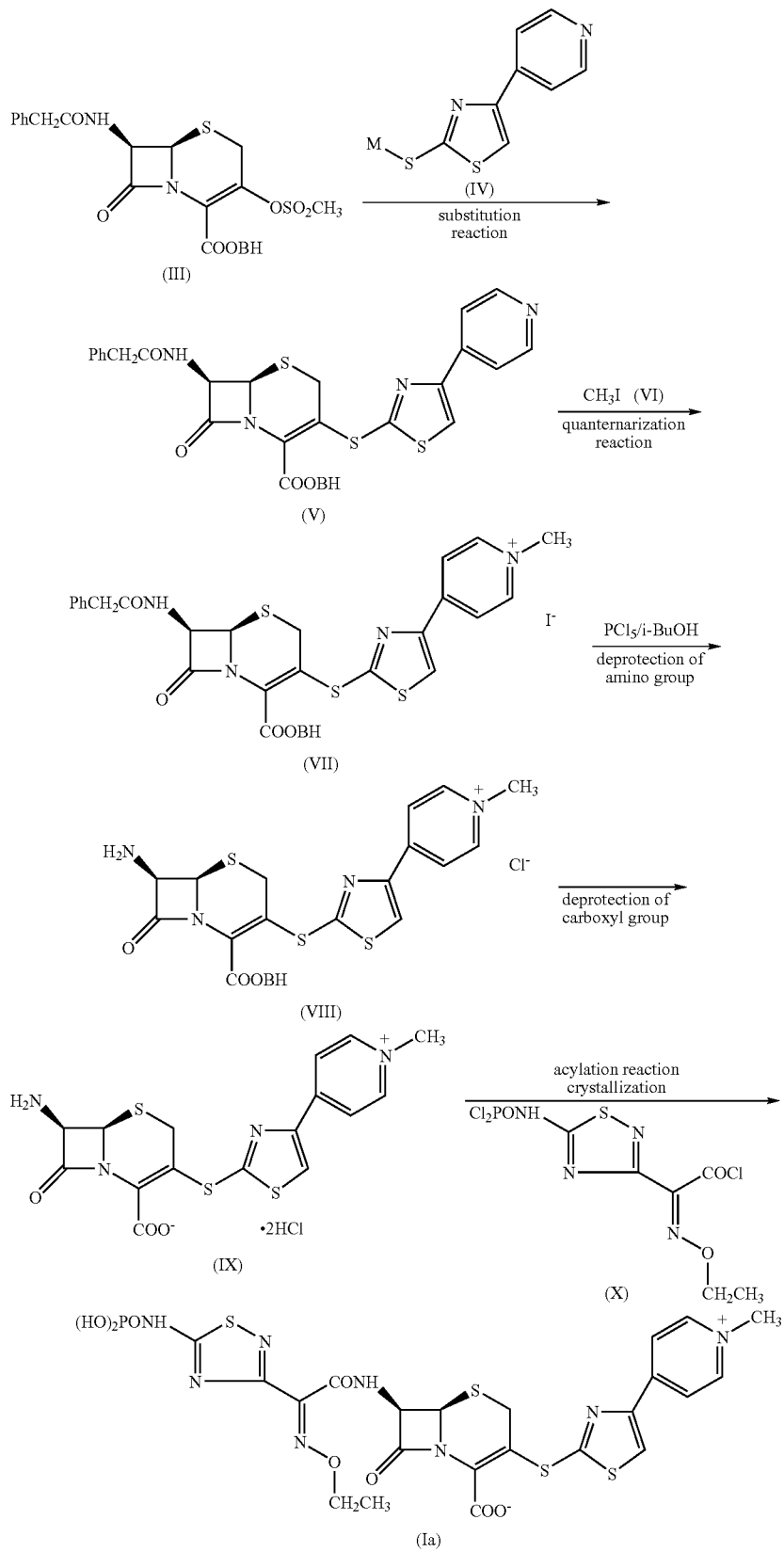

In the formulas (III), (V) and (VII), Ph shows phenyl group, BH shows benzhydryl group, in the formula (VIII), BH shows benzhydryl group, in the formula (IV), M shows alkali metal atom such as lithium, sodium, potassium and the like or alkaline earth metal atom such as magnesium, calcium, barium and the like, and i-BuOH shows isobutanol.

First, compound (III) and a compound of the formula (IV) [hereinafter referred to simply as compound (IV)] are reacted to give a compound of the formula (V) [hereinafter referred to simply as compound (V)]. The compound (III) is a known compound, and described in, for example, J. Org. Chem. 1989, 54, 4962-4966. This reaction is generally carried out in the presence of a solvent, and preferably carried out in an inert solvent such as hydrocarbons (e.g., toluene and the like), esters (e.g., ethyl acetate and the like), ketones (e.g., acetone and the like), halogenated hydrocarbons (e.g., chloroform, dichloromethane and the like), ethers (e.g., diethyl ether, tetrahydrofuran, dioxane and the like), nitrites (e.g., acetonitrile and the like), alcohols (e.g., methanol, ethanol, n-propanol and the like), amides (e.g., dimethylformamide, dimethylacetamide and the like), sulfoxides (e.g., dimethyl sulfoxide and the like), and the like. A mixture of 2 or 3 kinds of these solvents may be used as a solvent, and a mixture of the above-mentioned solvent with water can be also used as a solvent. Of these, tetrahydrofuran, acetonitrile, methanol and the like are preferable, particularly tetrahydrofuran, methanol and a mixture of the two are preferable. The amount of compound (IV) to be used is generally 1 to 3 mol, preferably 1 to 2 mol, per 1 mol of compound (III). The reaction temperature is from −40° C. to 80° C., preferably from −20° C. to 50° C. The reaction time is 5 min-12 hr, preferably 30 min-8 hr. Where necessary, a base and a salt can be added to this reaction, which can accelerate the reaction. Examples of such base and salts include inorganic bases such as sodium hydroxide, potassium hydroxide, sodium carbonate, potassium carbonate, sodium hydride and the like, alkoxides such as sodium methoxide, t-butoxypotassium, t-butoxysodium and the like, and organic amines such as trialkylamine (e.g., triethylamine, ethyldiisopropylamine and the like). Of these, sodium hydroxide and sodium methoxide are preferable. As the salt, quaternary ammonium salt such as tetrabutylammonium salt, and the like are used.

The compound (VII) can be produced by reacting compound (V) and reagent for forming quaternary ammonium such as iodomethane represented by the formula (VI) [hereinafter referred to simply as compound (VI)] and the like. This reaction is generally carried out in the presence of a solvent. Examples of the solvent generally include inert solvents such as hydrocarbons (e.g., toluene and the like), ketones (e.g., acetone and the like), halogenated hydrocarbons (e.g., chloroform, dichloromethane and the like), ethers (e.g., diethyl ether, tetrahydrofuran, dioxane and the like), nitriles (e.g., acetonitrile and the like), alcohols (e.g., methanol, ethanol, n-propanol and the like), amides (e.g., dimethylformamide, dimethylacetamide and the like), sulfoxides (e.g., dimethyl sulfoxide and the like) and the like. A mixture of 2 or 3 kinds of these solvents may be used as a solvent, and a mixture of the above-mentioned solvent with water can be also used as a solvent. Of these, tetrahydrofuran, dimethylformamide, acetonitrile and dimethyl sulfoxide are preferable, particularly tetrahydrofuran and dimethylformamide are preferable. The amount of reagent for forming quaternary ammonium to be used is generally 1-20 mol, preferably 1-10 mol, per 1 mol of compound (V). The reaction temperature is from −5° C. to 80° C., preferably from 0° C. to 50° C. The reaction time is 30 min-48 hr, preferably 2 hr-20 hr.

A compound represented by the formula (VIII) [hereinafter referred to simply as compound (VIII)] can be produced by subjecting compound (VII) to deprotection of amino group. This reaction is carried out using 1-10 mol, preferably 1-5 mol, of phosphorus pentachloride and 1-10 mol, preferably 1-5 mol, of tertiary amine (e.g., pyridine, N,N-dimethylaniline, picoline, lutidine and the like), relative to compound (VII), which are reacted in an inert solvent and reacting with 2-200 mol, preferably 3-125 mol, of alcohols (e.g., methanol, ethanol, isobutanol, isopropyl alcohol and the like). Preferable tertiary amine is exemplified by pyridine and N,N-dimethylaniline, and pyridine is particularly preferable. Preferable alcohol is exemplified by methanol, ethanol and isobutanol, and methanol and isobutanol are particularly preferable. Examples of the inert solvent generally include hydrocarbons (e.g., toluene and the like), esters (e.g., ethyl acetate and the like), ketones (e.g., acetone and the like), halogenated hydrocarbons (e.g., chloroform, dichloromethane and the like), ethers (e.g., diethyl ether, tetrahydrofuran, dioxane and the like), nitrites (e.g., acetonitrile and the like), amides (e.g., dimethylformamide, dimethylacetamide and the like), and sulfoxides (e.g., dimethyl sulfoxide and the like). A mixture of 2 or 3 kinds of these solvents may be used as a solvent. Of these, halogenated hydrocarbons such as chloroform, dichloromethane and the like are preferable, and dichloromethane is particularly preferable. The reaction temperature is from −40° C. to 80° C., preferably from −20° C. to 50° C. The reaction time is 30 min-48 hr, preferably 2 hr-24 hr.

Then, compound (VIII) is subjected to deprotection of carboxyl group to give a compound of the formula (IX) [hereinafter referred to simply as compound (IX)]. This reaction is generally carried out using an acid in a solvent. Examples of the solvent generally include inert solvents such as hydrocarbons (e.g., toluene and the like), ketones (e.g., acetone and the like), halogenated hydrocarbons (e.g., chloroform, dichloromethane and the like), ethers (e.g., diethyl ether, tetrahydrofuran, dioxane and the like), nitriles (e.g., acetonitrile and the like), esters (e.g., ethyl acetate and the like), alcohols (e.g., methanol, ethanol, n-propanol and the like), amides (e.g., dimethylformamide, dimethylacetamide and the like), sulfoxides (e.g., dimethyl sulfoxide and the like) and the like. A mixture of 2 or 3 kinds of these solvents may be used as a solvent. Of these, halogenated hydrocarbons such as chloroform, dichloromethane and the like, nitrites such as acetonitrile and the like, and esters such as ethyl acetate and the like are preferable, and acetonitrile, ethyl acetate and a mixture of the two are particularly preferable. As the acid, hydrochloric acid or trifluoroacetic acid is preferable, and hydrochloric acid is particularly preferable. The amount of the acid to be used is 2-200 mol, preferably 3-50 mol, relative to compound (VIII). In this case, anisole, phenol and the like are preferably added as a cation scavenger to accelerate the reaction. The reaction temperature is from −40° C. to 80° C., preferably from −20° C. to 50° C. The reaction time is 30 min-48 hr, preferably 2 hr-24 hr.

The compound (IX) obtained by this production method is generally obtained as an addition salt with one or two acids, and can be taken out from an organic solvent, water or a mixture of the both as a crystal of an addition salt with one or two acids. As the acid of the addition salt with one or two acids, mineral acid and organic acid are mentioned. Of these, hydrochloric acid, sulfuric acid and trifluoroacetic acid are preferable, and hydrochloric acid is particularly preferable. The organic solvent to be used is exemplified by the aforementioned inert solvents. Of those, acetonitrile, ethyl acetate, ethanol, dioxane and tetrahydrofuran are preferable, and acetonitrile, ethyl acetate and ethanol are particularly preferable.

Then, compound (IX) and a compound represented by the formula (X) [hereinafter referred to simply as compound (X)] are reacted to give compound (Ia).

As the compound (IX), a crystal of an acid addition salt is preferably used. In this reaction, generally 1-5 mol, preferably 1-2 mol, of compound (X) is reacted with 1 mol of compound (IX) in the presence of an acid scavenger to capture the acid generated during the reaction, in a solvent that does not inhibit the reaction. As the solvent, for example, tetrahydrofuran, acetonitrile, dioxane, acetone and a mixture of these solvents with water are preferable, and acetonitrile, tetrahydrofuran, a mixture of acetonitrile with water, and a mixture of tetrahydrofuran with water are particularly preferable. Examples of the acid scavenger include ones generally used such as salts (e.g., sodium hydrogencarbonate, sodium carbonate, potassium carbonate, sodium acetate, potassium acetate, sodium phosphate and the like), tertiary amines (e.g., triethylamine, tripropylamine, tributylamine, ethyldiisopropylamine, pyridine, lutidine, N,N-dimethylaniline, N-methylpiperidine, N-methylpyrrolidine, N-methylmorpholine and the like), alkylene oxides (e.g., propyleneoxide, epichlorohydrin and the like) and the like. Two or three therefrom may be used in a mixture. Of these, a combination of sodium hydrogencarbonate, sodium carbonate, sodium acetate, triethylamine or sodium acetate with triethylamine is preferable, and particularly a combination of sodium hydrogencarbonate, sodium acetate, triethylamine or sodium acetate with triethylamine is preferable. In this reaction, a dichlorophosphoryl group is successively hydrolyzed into phosphono group. The reaction temperature is from −40° C. to 80° C., preferably from −20° C. to 50° C. The reaction time is 20 min-48 hr, preferably 30 min-24 hr. The compound (X) can be synthesized by the method described in JP-A-11-255772 from the corresponding compound represented by the formula (XI) [hereinafter referred to simply as compound (XI)] and phosphorus pentachloride.

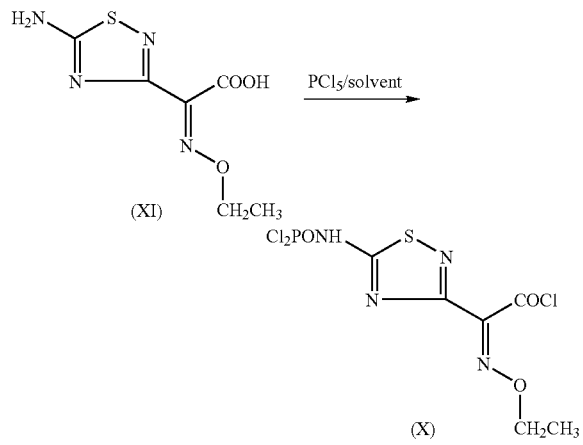

In this reaction, 1-5 mol, preferably 1 to 3 mol, of phosphorus pentachloride is generally reacted with 1 mol of compound (XI) in a solvent. As the solvent, tetrahydrofuran, ethyl acetate, isopropyl ether, dioxane, toluene and a mixture of these are preferable, and tetrahydrofuran, ethyl acetate, isopropyl ether and a mixture of these are particularly preferable. The reaction temperature is from −40° C. to 60° C., preferably from −10° C. to 25° C. The reaction time is 10 min-8 hr, preferably 20 min-4 hr. For isolation after reaction, a general method comprising extraction with water, or a method comprising directly adding a poor solvent or a poor solvent and water to the reaction mixture to obtain precipitated solid can be utilized. The poor solvent to be added is preferably toluene, isopropyl ether, n-hexane, cyclohexane or a mixture of these, particularly preferably toluene, isopropyl ether, n-hexane or a mixture of these.

EXAMPLES

The present invention is explained in detail by referring to the following Reference Examples, Examples and Experimental Examples, which are mere examples and do not limit the present invention. The present invention may be modified within the range that does not deviate from the scope of the present invention.

In the following Reference Examples, Examples and Experimental Examples, room temperature means 10-25° C.

The melting point was measured using YANAKO MP-J3. The $^1$H-NMR spectrum was measured using tetramethylsilane (CDCl$_3$, DMSO-d$_6$) or sodium 3-trimethylsilyl-propionate-2,2,3,3-d$_4$(D$_2$O) as an internal standard, and using VARIAN Gemini-200 (200 MHz), and all δ values are shown in ppm.

For ultrasonic treatment, SHARP UT-204 (water bath type) and TAITEC VP-60 (horn type) were used.

As the silica gel for column, kieselgel 60 (70-230 mesh, manufactured by Merck & Co., Inc.) was used. The column packing material ODS for HPLC was manufactured by YMC Co., Ltd., and Diaion HP-20SS and SP-207 were manufactured by Mitsubishi Chemical Corporation.

Elution in the column chromatography was carried out while monitoring with TLC (Thin Layer Chromatography) or HPLC. In the TLC monitoring, 60F254 manufactured by Merck & Co., Inc. was used as the TLC plate, as the developing solvent, a solvent wherein the objective compound is developed in the range of Rf value of 0.1-0.8 or a solvent similar thereto, and as the detection method, UV detection method was employed. For mixed solvents, the numeral value in the parenthesis is a mixing ratio in volume of each solvent. The % for a solution indicates the number of g (grams) in 100 mL of the solution. In Reference Examples and Examples, the symbols mean the following.

s: singlet
d: doublet
t: triplet
q: quartet
ABq: AB type quartet
dd: double doublet
m: multiplet
J: coupling constant Example 1 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (100 mg, 0.151 mmol) was suspended in a mixture of distilled water for injection (0.5 mL) and acetic acid (0.5 mL), and dissolved by ultrasonication. This solution was stood overnight at room temperature. The precipitated crystals were pulverized with a spatula and collected by filtration. The crystals were washed with distilled water for injection (1.2 mL). Using molecular sieves 3A (1/16) as a drying agent, the crystals were dried under reduced pressure until they reached a constant weight to give a seed crystal. yield: 79 mg (73%)

melting point: 221-223° C. (decomposition)

3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (350 mg, 0.51 mmol) was suspended in a mixture of distilled water for injection (2.38 mL) and acetic acid (2.38 mL), and dissolved by ultrasonication. The seed crystal was added and crystallization was allowed to take place with stirring at room temperature for 4 hr, which was followed by standing in a refrigerator overnight. A mixture (0.8 mL) of distilled water for injection/acetic acid (1:1) was added and the precipitated crystals were pulverized with a spatula, collected by filtration, washed 3 times with a mixture (0.8 mL) of distilled water for injection/acetic acid (1:1) and washed 5 times with distilled water for injection (1.0 mL). Using molecular sieves 3A (1/16) as a drying agent, the crystals were dried under reduced pressure until they reached a constant weight. yield: 260 mg (68%)

melting point: 221-223° C. (decomposition) Anal Calcd for $C_{24}H_{25}N_8O_{10}S_4P \cdot 1.0H_2O$: C, 37.79; H, 3.57; N, 14.69; P, 4.06. Found: C, 37.97; H, 3.30; N, 14.37; P, 3.88. $^1$H-NMR (DMSO-$d_6$) δ: 1.24 (3H,t,J=7 Hz), 1.91 (3H,s), 3.58, 3.95 (2H,ABq,J=17 Hz), 4.17 (2H,q,J=7 Hz), 4.34 (3H,s), 5.32 (1H,d,J=5 Hz), 5.92 (1H,dd,J=5&8 Hz), 8.51 (2H,d,J=6 Hz), 8.99 (3H,m), 9.30 (1H,m), 9.70 (1H,d,J=8 Hz).

IR (KBr) cm$^{-1}$: 3202, 1755, 1668, 1645, 1537, 1392, 1273, 1039.

In FIG. 1, a powder X-ray diffraction spectrum (Cu, 40 kV, 50 mA) of the compound obtained in this Example is shown, wherein the transverse axis shows diffraction angle (2θ) and the vertical axis shows peak intensity.

Example 2 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (60 g, 87.6 mmol) was suspended in a mixture of distilled water for injection (408 mL) and acetic acid (408 mL), and dissolved by ultrasonication. The seed crystal obtained in Example 1 was added, and crystallization was allowed to take place with stirring at room temperature for 5 hr, which was followed by standing in a refrigerator overnight. The precipitated crystals were collected by filtration, washed twice with a mixture (68 mL) of distilled water for injection/acetic acid (1:1) and 5 times with distilled water for injection (85 mL). Using molecular sieves 3A (1/16) as a drying agent, the crystals were dried under reduced pressure until they reached a constant weight. yield: 44.5 g (68%)

melting point: 221-223° C. (decomposition)

Anal Calcd for $C_{24}H_{25}N_8O_{10}S_4P \cdot 1.0H_2O$: C 37.79, H 3.57, N, 14.69; P 4.06. Found: C 37.97, H 3.30, N, 14.37, P 3.88. $^1$H-NMR (DMSO-$d_6$) δ: 1.24 (3H,t,J=7 Hz), 1.91 (3H, s), 3.58, 3.95 (2H,ABq,J=17 Hz), 4.17 (2H,q,J=7 Hz), 4.34 (3H,s), 5.32 (1H,d,J=5 Hz), 5.92 (1H,dd,J=5&8 Hz), 8.51 (2H,d,J=6 Hz), 8.99 (3H,m), 9.30 (1H,m), 9.70 (1H,d,J=8 Hz). IR (KBr) cm$^{-1}$: 3202, 1755, 1668, 1645, 1537, 1392, 1273, 1039.

Example 3 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (58 g, 84.7 mmol) was suspended in a mixture of distilled water for injection (208 mL) and acetic acid (208 mL), and dissolved by ultrasonication. The seed crystal obtained in Example 1 was added and the mixture was subjected to ultrasonication (horn type ultrasonic device) at room temperature for 30 min. A mixture (108 mL) of distilled water for injection/acetic acid (1:1) was added, the crystals were pulverized and the mixture was stirred at room temperature for 1 hr. A mixture (108 mL) of distilled water for injection/acetic acid (1:1) was added, the crystals were pulverized and the mixture was stirred at room temperature for 1 hr. The above-mentioned step was repeated, which was followed by standing in a refrigerator overnight. The precipitated crystals were collected by filtration, washed twice with a mixture (120 mL) of distilled water for injection/acetic acid (1:1), and 5 times with distilled water for injection (120 mL). Using diphosphorus pentaoxide as a drying agent, the crystals were dried under reduced pressure until they reached a constant weight. yield: 42.6 g (68%)

melting point: 221-223° C. (decomposition)

Anal Calcd for $C_{24}H_{25}N_8O_{10}S_4P \cdot 1.0H_2O$: C 37.79, H, 3.57, N 14.69, P 4.06. Found: C 37.97, H 3.30, N, 14.37, P, 3.88. $^1$H-NMR (DMSO-$d_6$) δ: 1.24 (3H,t,J=7 Hz), 1.91 (3H, s), 3.58, 3.95 (2H,ABq,J=17 Hz), 4.17 (2H,q,J=7 Hz), 4.34 (3H,s), 5.32 (1H,d,J=5 Hz), 5.92 (1H,dd,J=5&8 Hz), 8.51 (2H,d,J=6 Hz), 8.99 (3H,m), 9.30 (1H,m), 9.70 (1H,d,J=8 Hz). IR (KBr) cm$^{-1}$: 3202, 1755, 1668, 1645, 1537, 1392, 1273, 1039.

Example 4 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (2.0 g, 2.92 mmol) was suspended in a mixture of distilled water for injection (7.5 mL) and acetic acid (7.5 mL), and dissolved by ultrasonication. The solution was stood at room temperature for 16 hr to allow crystallization to take place. The crystals were collected by filtration, and washed twice with a mixture (5 mL) of distilled water for injection/acetic acid (1:1), and 5 times with distilled water for injection (5 mL). Using molecular sieves 3A (1/16) as a drying agent, the crystals were dried under reduced pressure until they reached a constant weight. yield: 1.41 g (65%)

melting point: 221-223° C. (decomposition) Anal Calcd for $C_{24}H_{25}N_8O_{10}S_4P \cdot 1.0H_2O$: C 37.79, H 3.57, N, 14.69; P 4.06. Found: C 37.97, H 3.30, N, 14.37, P 3.88. $^1$H-NMR (DMSO-$d_6$) δ: 1.24 (3H,t,J=7 Hz), 1.91 (3H,s), 3.58, 3.95 (2H,ABq,J=17 Hz), 4.17 (2H,q,J=7 Hz), 4.34 (3H,s), 5.32 (1H,d,J=5 Hz), 5.92 (1H,dd,J=5&8 Hz), 8.51 (2H,d,J=6 Hz), 8.99 (3H,m), 9.30 (1H,m), 9.70 (1H,d,J=8 Hz). IR (KBr) cm$^{-1}$: 3202, 1755, 1668, 1645, 1537, 1392, 1273, 1039.

Example 5 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with propionic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (100 mg, 0.15 mmol) was suspended in a mixture of distilled water for injection (0.5 mL) and propionic acid (0.5 mL), and dissolved by ultrasonication. Crystallization was allowed to take place with stirring at room temperature for 2.5 hr. The precipitated crystals were collected by filtration, and washed with distilled water for injection (0.5 mL). Using diphosphorus pentaoxide as a drying agent, the crystals were dried under reduced pressure until they reached a constant weight. yield: 97 mg (88%)

melting point: 227-230° C. (decomposition) Anal Calcd for $C_{25}H_{27}N_8O_{10}S_4P.1.0H_2O$: C 38.66, H 3.76, N 14.16, Found: C 38.51, H 3.76, N 14.16. $^1$H-NMR (DMSO-$d_6$) δ: 0.99 (3H,t,J=7.6 Hz), 1.24 (3H,t,J=7 Hz), 2.21 (2H,q,J=7.6 Hz), 3.59, 3.95 (2H,ABq,J=18 Hz), 4.17 (2H,q,J=7 Hz), 4.33 (3H,s), 5.31 (1H,d,J=5 Hz), 5.91 (1H,dd,J=5&8 Hz), 8.52, 8.98 (each 2H,d,J=6 Hz), 9.00 (1H,s), 9.24 (1H,m), 9.68 (1H,d,J=8 Hz). IR (KBr) cm$^{-1}$: 3088, 1757, 1668, 1537, 1392, 1234, 1190, 1043.

Figure 2:
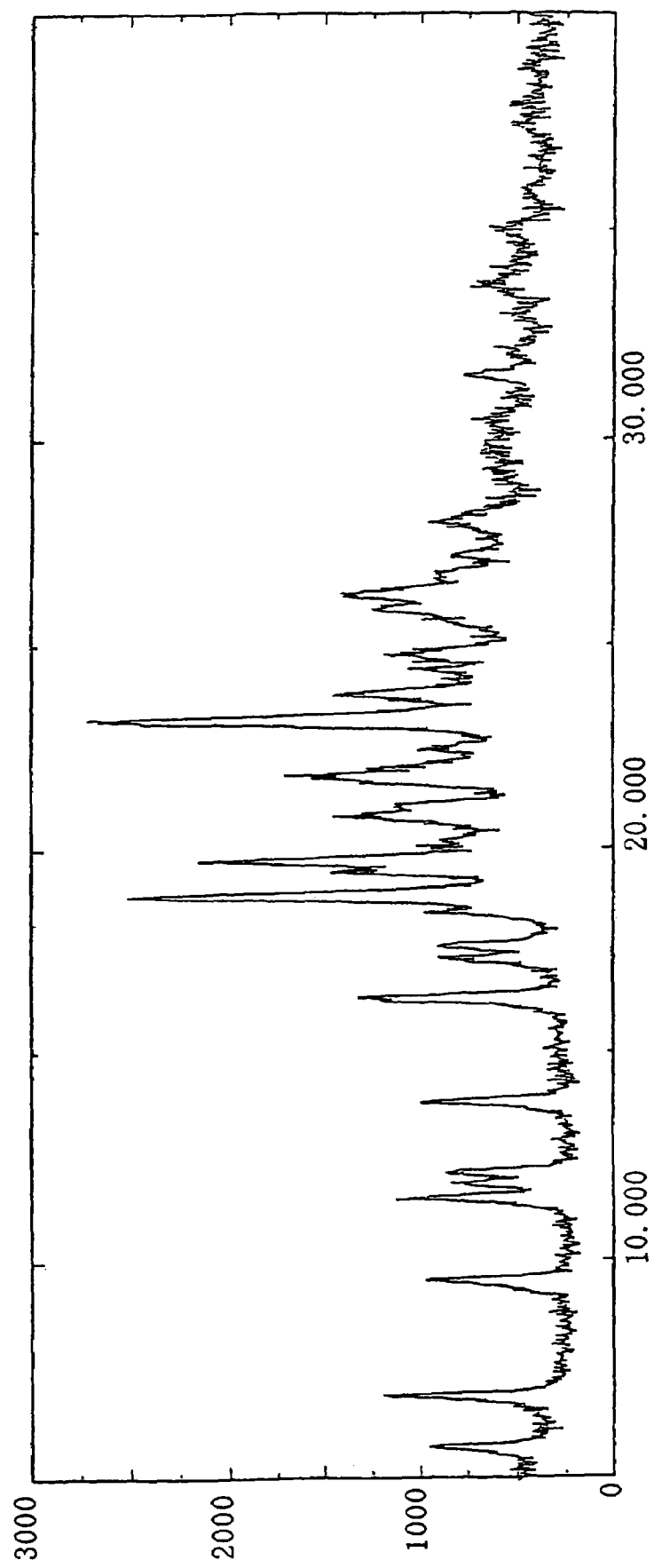
FIG. 2 shows a powder X-ray diffraction spectrum (Cu, 40 kV, 50 mA) of the compound obtained in Example 5, wherein the transverse axis shows a diffraction angle (2θ) and the vertical axis shows a peak intensity.

In FIG. 2, a powder X-ray diffraction spectrum (Cu, 40 kV, 50 mA) of the compound obtained in this Example is shown, wherein the transverse axis shows diffraction angle (2θ) and the vertical axis shows peak intensity.

Example 6 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetonitrile 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (100 mg, 0.15 mmol) was suspended in a mixture of distilled water for injection (1.2 mL) and acetonitrile (1.2 mL), and was dissolved by ultrasonication and warming to 50° C. This solution was stood at room temperature overnight. The precipitated crystals were collected by filtration, washed with water/acetonitrile (4:1), and air-dried to a constant weight. yield: 63 mg (59%)

melting point: 210-215° C. (decomposition) $^1$H-NMR (DMSO-$d_6$) δ: 1.23 (3H,t,J=7 Hz), 2.07 (3H,s), 3.58, 3.95 (2H,ABq,J=17 Hz), 4.17 (2H,q,J=7 Hz), 4.33 (3H,s), 5.32 (1H,d,J=5 Hz), 5.91 (1H,dd,J=5&8 Hz), 8.51 (2H,d,J=6 Hz), 8.99 (3H,m), 9.34 (1H,m), 9.71 (1H,d,J=8 Hz).

Figure 3:
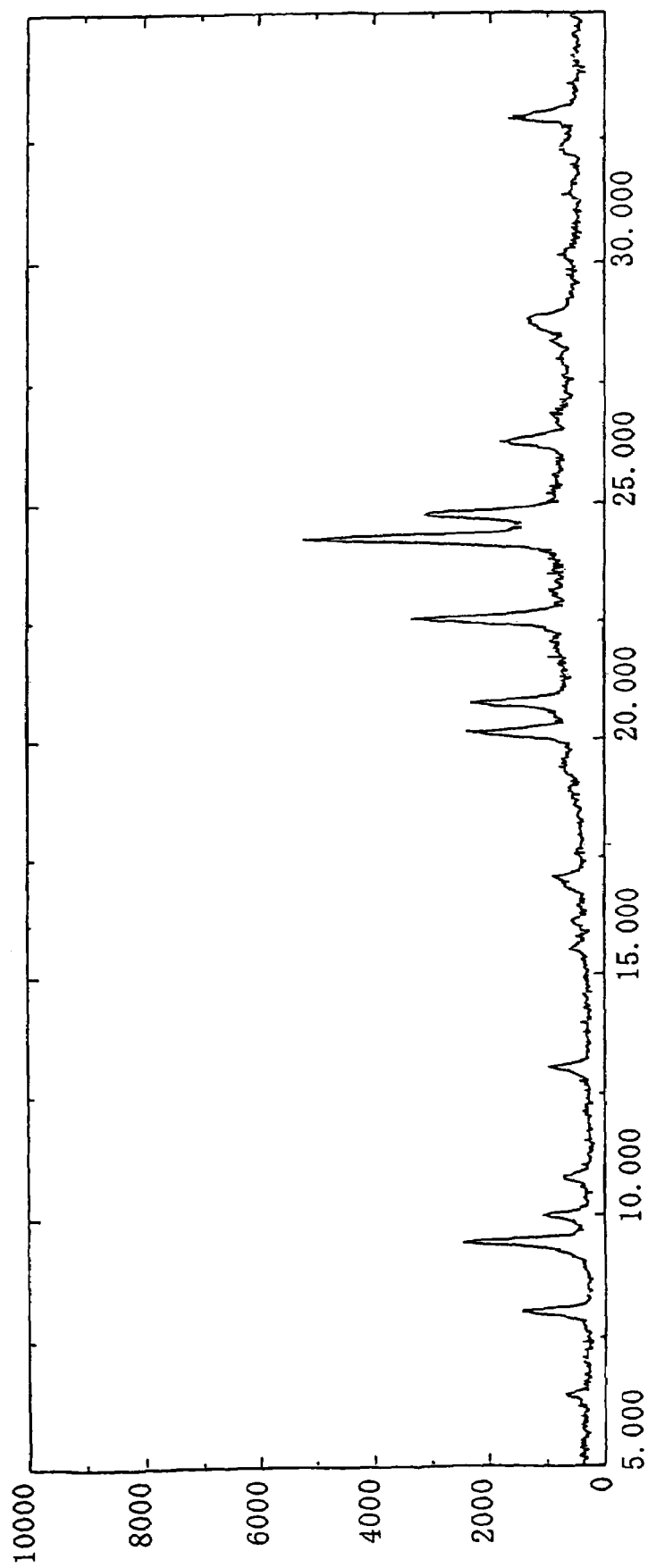
FIG. 3 shows a powder X-ray diffraction spectrum (Cu, 40 kV, 50 mA) of the compound obtained in Example 6, wherein the transverse axis shows a diffraction angle (2θ) and the vertical axis shows a peak intensity.

In FIG. 3, a powder X-ray diffraction spectrum (Cu, 40 kV, 50 mA) of the compound obtained in this Example is shown, wherein the transverse axis shows diffraction angle (2θ) and the vertical axis shows peak intensity.

Example 7 disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate 7β-Amino-3-[4-(1-methyl-4-pyridinio)-2-thiazolylthio]-3-cephem-4-carboxylate (400 mg, 0.834 mmol) was dissolved in distilled water (24 mL) with stirring. 2M Aqueous sodium acetate solution (4.18 mL) was added with stirring under ice-cooling. 2-(5-Dichlorophosphorylamino-1,2,4-thiadiazol-3-yl)-2(Z)-ethoxyiminoacetyl chloride (294 mg, 0.836 mmol) was dissolved in acetonitrile (2 mL) and added at once to the above-mentioned reaction mixture with stirring under ice-cooling. The mixture was stirred at room temperature for 1 hr 15 min. Ethyl acetate (20 mL) was added to the reaction mixture for partitioning. The separated aqueous layer was passed through a membrane filter (0.45 μm). The filtrate was concentrated to near dryness under reduced pressure. The residual solid was dissolved in distilled water (4 mL). Ethanol (4 mL) was added and the mixture was stirred. The crystals gradually precipitated. Ethanol (4 mL) was gradually added to promote crystal growth. After the mixture was stood under ice-cooling for 30 min, the precipitated crystals were collected by filtration. The crystals were washed successively with distilled water/ethanol (1:2, 4 mL) and ethanol (4 mL), and air-dried on a funnel. yield: 554 mg (91%)

melting point: 217-222° C. (decomposition) $^1$H-NMR (DMSO-$d_6$:$D_2O$=8:2) δ: 1.27 (3H,t,J=7 Hz), 3.40, 3.89 (2H, ABq,J=17 Hz), 4.24 (2H,q,J=7 Hz), 4.30 (3H,s), 5.23 (1H,d, J=5 Hz), 5.79 (1H,d,J=5 Hz), 8.37, 8.77 (each 2H,d,J=7 Hz), 8.66 (1H,s). IR (KBr) cm$^{-1}$: 3184, 1761, 1643, 1614, 1537, 1390, 1346, 1190, 1041.

Figure 4:
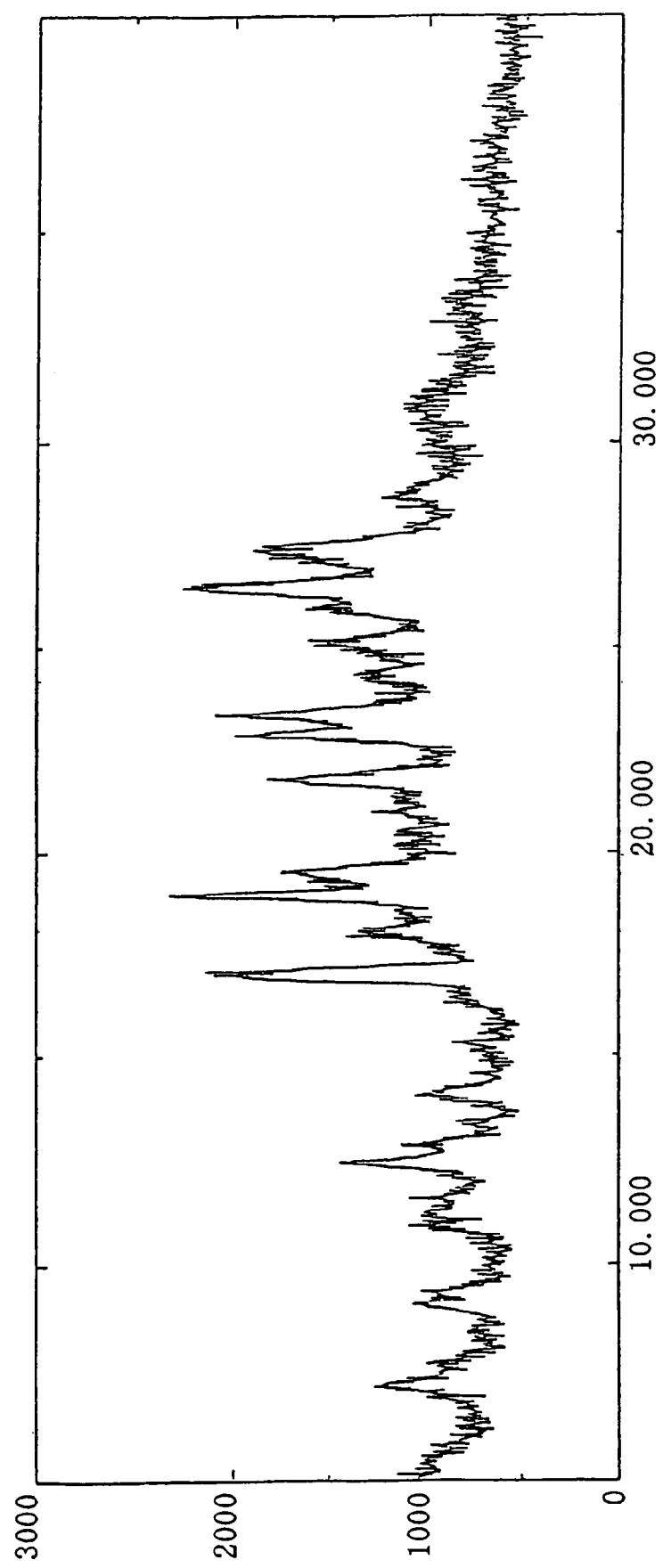
FIG. 4 shows a powder X-ray diffraction spectrum (Cu, 40 kV, 50 mA) of the compound obtained in Example 7, wherein the transverse axis shows a diffraction angle (2θ) and the vertical axis shows a peak intensity.

In FIG. 4, a powder X-ray diffraction spectrum (Cu, 40 kV, 50 mA) of the compound obtained in this Example is shown, wherein the transverse axis shows diffraction angle (2θ) and the vertical axis shows peak intensity.

Example 8 disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate 7β-Amino-3-[4-(1-methyl-4-pyridinio)-2-thiazolylthio]-3-cephem-4-carboxylate (60 g, 125 mmol) was dissolved in distilled water (3.6 L) with stirring. 2M Aqueous sodium acetate solution (700 mL) was added with stirring under ice-cooling. 2-(5-Dichlorophosphorylamino-1,2,4-thiadiazol-3-yl)-2(Z)-ethoxyiminoacetyl chloride (52.8 g, 150 mmol) was dissolved in acetonitrile (300 mL) and added once to the above-mentioned reaction mixture with stirring under ice-cooling. The mixture was stirred at room temperature for 1 hr. Ethyl acetate (3 L) was added to the reaction mixture for partitioning. The aqueous layer was separately taken and passed through a membrane filter (0.45 μm). The filtrate was concentrated under reduced pressure to 600 mL. Ethanol (600 mL) was added and the crystals gradually precipitated. Ethanol (600 mL) was gradually added and the mixture was stood under ice-cooling for 30 min. The precipitated crystals were collected by filtration and washed successively with distilled water/ethanol (1:2, 450 mL) and ethanol (600 mL). After washing, they were air-dried on a funnel. yield: 128.7 g (quantitative)

melting point: 217-222° C. (decomposition) $^1$H-NMR (DMSO-d$_6$:D$_2$O=8:2) δ: 1.27 (3H,t,J=7 Hz), 3.40, 3.89 (2H, ABq,J=17 Hz), 4.24 (2H,q,J=7 Hz), 4.30 (3H,s), 5.23 (1H,d, J=5 Hz), 5.79 (1H,d,J=5 Hz), 8.37, 8.77 (each 2H,d,J=7 Hz), 8.66 (1H,s). IR (KBr) cm$^{-1}$: 3184, 1761, 1643, 1614, 1537, 1390, 1346, 1190, 1041.

Example 9 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (4.0 g, 5.84 mmol) was suspended in distilled water for injection (12 mL), 2M aqueous sodium acetate solution (5.84 mL) was added, and the mixture was dissolved. Acetic acid (24 mL) and then 1M sulfuric acid (5.78 mL) were added and a seed crystal was added. The mixture was stood at room temperature for 24 hr. The precipitated crystals were pulverized, and collected by filtration. The obtained crystals were washed 3 times with a mixture (4 mL) of distilled water for injection/acetic acid (1:1), and 5 times with distilled water for injection (4 mL). Using molecular sieves 3A (1/16) as a drying agent, the crystals were dried under reduced pressure until they reached a constant weight. yield: 1.48 g (38%)

melting point: 221-223° C. (decomposition) Anal Calcd for C$_{24}$H$_{25}$N$_8$O$_{10}$S$_4$P.1.0H$_2$O: C 37.79, H 3.57, N 14.69, P 4.06. Found: C 37.97, H 3.30, N 14.37; P 3.88. $^1$H-NMR (DMSO-d$_6$) δ: 1.24 (3H,t,J=7 Hz), 1.91 (3H,s), 3.58, 3.95 (2H,ABq,J=17 Hz), 4.17 (2H,q,J=7 Hz), 4.34 (3H,s), 5.32 (1H,d,J=5 Hz), 5.92 (1H,dd,J=5&8 Hz), 8.51 (2H,d,J=6 Hz), 8.99 (3H,m), 9.30 (1H,m), 9.70 (1H,d,J=8 Hz). IR (KBr) cm$^{-1}$: 3202, 1755, 1668, 1645, 1537, 1392, 1273, 1039.

Example 10 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid In the same manner as in Example 9 except that distilled water for injection was changed to 5% glucose injection, the title compound was obtained. yield: 1.34 g (35%)

Example 11 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid In the same manner as in Example 9 except that distilled water for injection was changed to 20% D-mannitol injection, the title compound was obtained. yield: 1.88 g (48%)

Example 12 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (4.0 g, 5.84 mmol) was suspended in 5% glucose injection (12 mL), and 2M aqueous sodium acetate solution (5.84 mL) was added for dissolution. Acetic acid (24 mL) and then 1M sulfuric acid (5.78 mL) were added and a seed crystal was added. The mixture was stirred at room temperature for 24 hr. The precipitated crystals were collected by filtration, and the obtained crystals were washed 3 times with a mixture (4 mL) of distilled water for injection/acetic acid (1:1) and 5 times with distilled water for injection (4 mL). Using molecular sieves 3A (1/16) as a drying agent, the crystals were dried under reduced pressure until they reached a constant weight. yield: 2.01 g (52%)

The physicochemical data were the same as those in Example 1.

Example 13 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid In the same manner as in Example 12 except that 2M aqueous sodium acetate was changed to 2M aqueous ammonium acetate, the title compound was obtained. yield: 1.44 g (37%)

Example 14 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid In the same manner as in Example 12 except that distilled water for injection was changed to 20% D-mannitol injection, the title compound was obtained. yield: 2.33 g (60%)

Example 15 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (10 g, 14.6 mmol) was suspended in 5% glucose injection (30 mL) and 2M aqueous sodium acetate solution (14.6 mL) was added for dissolution. Acetic acid (60 mL) and then 1M sulfuric acid (14.46 mL) were added and a seed crystal was added. The mixture was stirred at room temperature for 2 hr and stood for 22 hr. The precipitated crystals were pulverized and collected by filtration. The obtained crystals were washed 3 times with a mixture (10 mL) of distilled water for injection/acetic acid (1:1) and 5 times with distilled water for injection (10 mL).

Using molecular sieves 3A (1/16) as a drying agent, the crystals were dried under reduced pressure until they reached a constant weight. yield: 6.90 g (71%)

The physicochemical data were the same as those in Example 1.

Example 16 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (10 g, 14.6 mmol) was suspended in distilled water for injection (30 mL) and 2M aqueous sodium acetate solution (14.6 mL) was added for dissolution. Acetic acid (60 mL) and then 1M sulfuric acid (14.46 mL) were added and a seed crystal was added. The mixture was stirred at room temperature for 5 hr and stood for 1 hr. The precipitated crystals were collected by filtration. The obtained crystals were washed 3 times with a mixture (10 mL) of distilled water for injection/acetic acid (1:1) and 5 times with distilled water for injection (10 mL). Using molecular sieves 3A (1/16) as a drying agent, the crystals were dried under reduced pressure until they reached a constant weight. yield: 5.55 g (57%)

The physicochemical data were the same as those in Example 1.

Example 17 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid In the same manner as in Example 16 except that distilled water for injection was changed to 5% glucose injection, the title compound was obtained. yield: 5.70 g (59%)

Example 18 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid In the same manner as in Example 16 except that distilled water for injection was changed to 20% D-mannitol injection, the title compound was obtained. yield: 6.21 g (64%)

Example 19 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (80 g, 116.8 mmol) was gradually added to a mixture of 20% D-mannitol injection (160 mL) and 2M aqueous sodium acetate solution (116.8 mL) for dissolution. Acetic acid (400 mL) and then 1M sulfuric acid (115.7 mL) were added, and a seed crystal was added. The mixture was stirred at room temperature for 3 hr. The precipitated crystals were collected by filtration. The obtained crystals were washed 3 times with a mixture (80 mL) of distilled water for injection/acetic acid (1:1) and 5 times with distilled water for injection (160 mL). Using molecular sieves 3A (1/16) as a drying agent, the crystals were dried under reduced pressure until they reached a constant weight. yield: 50 g (64%)

The physicochemical data were the same as those in Example 1.

Example 20 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (1600 g, 2.34 mol) was dissolved in a solution of sodium acetate (428.2 g, 5.14 mol), D-mannitol (425.7 g, 2.34 mol) and distilled water for injection (6.1 L), and acetic acid (8 L) and 2M sulfuric acid (1864 mL, 3.73 mol) were added. The mixture was stirred at room temperature for 30 min, and a seed crystal (16 g) was added. The mixture was further stirred for 2 hr. The obtained crystals were collected by filtration, and washed with a mixture (20 L) of distilled water for injection/acetic acid (1:1). The crystals were through-flow dried until they reached a constant weight. yield: 1390 g (74%)

Example 21 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (94.8 g, 138 mmol) was dissolved in 25% aqueous ammonia (10.4 g, 153 mmol) and distilled water for injection (406 mL), and acetic acid (500 mL) and 10% sulfuric acid (88.3 g, 90 mmol) were added. The seed crystal (80 mg) was added and the mixture was stirred at room temperature for 2.5 hr. The mixture was stirred once every 30 min thereafter for the total of 5 hr, and stood overnight. A mixture (500 mL) of distilled water for injection/acetic acid (1:1) was added. The crystals were collected by filtration, and washed 3 times with a mixture (200 mL) of distilled water for injection/acetic acid (1:1). The crystals were through-flow dried until they reached a constant weight. yield: 75.5 g (71.5%)

The physicochemical data were the same as those in Example 1.

Example 22 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid 3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (10 g, 14.6 mol) was dissolved in a solution of 25% aqueous ammonia (2.18 g, 32.1 mmol), D-mannitol (2.66 g, 14.6 mol) and distilled water for injection (38 mL), and acetic acid (50 mL) and 2M sulfuric acid (12 mL, 24.0 mol) were added. The mixture was stirred at room temperature for 30 min, and a seed crystal (0.1 g) was added. The mixture was further stirred for 1.5 hr. The obtained crystals were collected by filtration, and washed twice with a mixture (50 mL) of distilled water for injection/acetic acid (1:1), twice with a mixture (50 mL) of distilled water for injection/acetic acid (1:4), and once with a mixture (50 mL) of ethanol/acetic acid (1:1). The crystals were through-flow dried until they reached a constant weight. yield: 6.53 g (60%)

The physicochemical data were the same as those in Example 1.

Example 23 crystal of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid An aqueous solution of disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate obtained by column chromatography according to the method of Reference Example 25 was concentrated under reduced pressure to give 52.2 g thereof (content 19.2%, 13.7 mmol). Acetic acid (52.2 mL) and 1M sulfuric acid (27.4 mL, 27.4 mmol) were added to the solution. A seed crystal was added, and the mixture was stirred at room temperature for 5 hr and stood for 1 hr. The crystals were collected by filtration, and washed with a mixture (100 mL) of distilled water for injection/acetic acid (1:1) and distilled water for injection (200 mL). The crystals were dried in vacuo until they reached a constant weight. yield: 7.02 g (68.8%)

Example 24

3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate To a solution of sodium acetate (1001 g, 12.2 mol) in distilled water for injection (15 L) was added 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate (3740 g, 5.46 mol) for dissolution. The mixture was passed through a 0.2 µm membrane filter, and washed with distilled water for injection (9 L). To a mixture of the filtrate and washing were added acetic acid (28 L) and then 2M sulfuric acid (4.35 L) and a seed crystal (3.74 g) was added. The mixture was stirred at 30° C. for 5 hr. The precipitated crystals were collected by filtration, and washed with a mixture (75 L) of distilled water for injection/acetic acid (1:1), a mixture (19 L) of distilled water for injection/acetic acid (1:4) and a mixture (19 L) of ethanol/acetic acid (1:1) with stirring. The air having a dew point of −5° C. was passed to dry the crystals. yield: 2011 g (49%)

Figure 5:
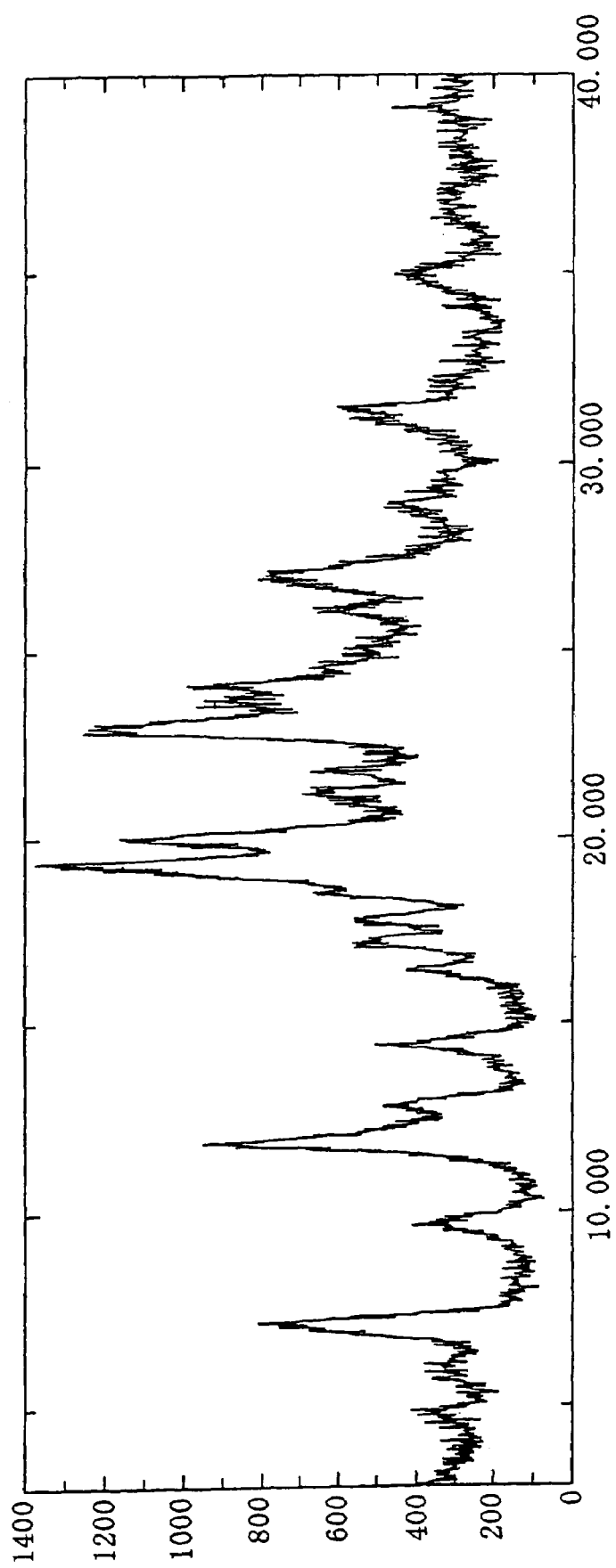
FIG. 5 shows a powder X-ray diffraction spectrum (Cu, 40 kV, 50 mA) of the compound obtained in Example 24, wherein the transverse axis shows a diffraction angle (2θ) and the vertical axis shows a peak intensity.

In FIG. 5, a powder X-ray diffraction spectrum (Cu, 40 kV, 50 mA) of the compound obtained in this Example is shown, wherein the transverse axis shows diffraction angle (2θ) and the vertical axis shows peak intensity.

Reference Example 1 benzhydryl 7β-amino-3-[4-(4-pyridyl)-2-thiazolylthio]-3-cephem-4-carboxylate

Benzhydryl 7β-phenylacetylamino-3-[4-(4-pyridyl)-2-thiazolylthio]-3-cephem-4-carboxylate (4.15 g, 6.0 mmol) was dissolved in dichloromethane (60 mL) and pyridine (0.726 mL, 9.0 mmol) and phosphorus pentachloride (1.87 g, 9.0 mmol) were successively added under ice-cooling. The mixture was stirred under ice-cooling for 1 hr. Isobutanol (8.0 mL) was added at once to the reaction mixture, and the mixture was stirred at room temperature for 1 hr. Isopropyl ether (300 mL) was added dropwise and the mixture was stirred for 10 min. The solvent was removed by decantation. The residual oil was suspended in ethyl acetate (600 mL) and saturated aqueous sodium hydrogencarbonate solution (200 mL) was added dropwise, after which the mixture was stirred for 15 min. The organic layer was separately taken, dried over magnesium sulfate and filtrated. The solvent was evaporated off under reduced pressure. Isopropyl ether (60 mL) was added to the residue, and the precipitated powder was collected by filtration, washed with isopropyl ether (20 mL) and dried under reduced pressure. yield: 3.18 g (95%)

$^1$H-NMR (DMSO-$d_6$) δ: 3.51, 3.77 (2H,ABq,J=18 Hz), 4.82 (1H,d,J=5 Hz), 5.02 (1H,d,J=5 Hz), 7.01 (1H,s), 7.2-7.5 (10H,m), 7.71 (1H,s), 7.73, 8.68 (each 2H,d,J=6 Hz).

Reference Example 2 benzhydryl 7β-t-butoxycarbonylamino-3-[4-(4-pyridyl)-2-thiazolylthio]-3-cephem-4-carboxylate Benzhydryl 7β-amino-3-[4-(4-pyridyl)-2-thiazolylthio]-3-cephem-4-carboxylate (3.0 g, 5.37 mmol) was suspended in tetrahydrofuran (40 mL) and dibutyl dicarbonate (2.34 g, 10.7 mmol) was added. The mixture was stirred at room temperature for 18 hr and concentrated under reduced pressure. The residue was dissolved in ethyl acetate (30 mL) and applied to silica gel column (30 g). The fractions containing the title compound eluted with ethyl acetate were collected, and the solvent was evaporated off under reduced pressure. Isopropyl ether (50 mL) was added to the residue, and the precipitated powder was collected by filtration, washed with isopropyl ether (10 mL) and dried under reduced pressure. yield: 1.4 g (40%)

$^1$H-NMR (CDCl$_3$) δ: 1.45 (9H,s), 3.51, 3.74 (2H,ABq, J=18 Hz), 5.04 (1H,d,J=5 Hz), 5.40 (1H,d,J=10 Hz), 5.69 (1H,dd,J=5&10 Hz), 7.00 (1H,s), 7.1-7.5 (10H,m), 7.70-7.74 (3H,m), 8.67 (2H,d,J=6 Hz).

Reference Example 3 benzhydryl 7β-t-butoxycarbonylamino-3-[4-(1-methyl-4-pyridinio)-2-thiazolylthio]-3-cephem-4-carboxylate iodide Benzhydryl 7β-t-butoxycarbonylamino-3-[4-(4-pyridyl)-2-thiazolylthio]-3-cephem-4-carboxylate (1.3 g, 1.97 mmol) was dissolved in dimethylformamide (2.6 mL) and iodomethane (1.23 mL, 19.7 mmol) was added. The mixture was stirred at room temperature for 5 hr. The reaction mixture was concentrated under reduced pressure and diethyl ether (100 mL) was added to the residue. The mixture was stirred for 10 min. The precipitated powder was collected by filtration, washed with diethyl ether (20 mL) and dried under reduced pressure. yield: 1.57 g (99%)

¹H-NMR (DMSO-d$_6$) δ: 1.41 (9H,s), 3.68, 3.97 (2H,ABq, J=18 Hz), 4.34 (3H,s), 5.29 (1H,d,J=5 Hz), 5.67 (1H,dd, J=5&8.6 Hz), 6.96 (1H,s), 7.1-7.5 (10H,m), 8.16 (1H,d,J=8.6 Hz), 8.53, 9.00 (each 2H,d,J=6.6 Hz), 9.02 (1H,s).

Reference Example 4

7β-amino-3-[4-(1-methyl-4-pyridinio)-2-thiazolylthio]-3-cephem-4-carboxylate.dihydrochloride Benzhydryl 7β-t-butoxycarbonylamino-3-[4-(1-methyl-4-pyridinio)-2-thiazolylthio]-3-cephem-4-carboxylate iodide (1.3 g, 1.62 mmol) was dissolved in acetonitrile (3 mL), and conc. hydrochloric acid (3 mL) was added. The mixture was stirred at 35-40° C. for 2 hr. The reaction mixture was concentrated under reduced pressure, and ethanol (30 mL) was added to the residue. The precipitated powder was collected by filtration, washed with ethanol (10 mL) and dried under reduced pressure. yield: 239 mg (31%)

¹H-NMR (DMSO-d$_6$) δ: 3.82, 3.96 (2H,ABq,J=18 Hz), 4.35 (3H,s), 5.27 (1H,d,J=5 Hz), 5.40 (1H,d,J=5 Hz), 8.61, 9.06 (each 2H,d,J=6 Hz), 9.16 (1H,s).

Reference Example 5

4-(4-pyridyl)-1,3-thiazole-2-thiol sodium salt 4-(4-Pyridyl)-1,3-thiazole-2-thiol (194 g, 1.0 mol, powder) was added to 8N aqueous sodium hydroxide solution (1.25 L, 10 mol) and the mixture was stirred for 30 min. The precipitated crystals were collected by filtration and washed with 8N aqueous sodium hydroxide solution (0.4 L). The obtained wet crystals were recrystallized from isopropyl alcohol (200 mL) to give the title compound (166 g, 0.77 mol) as yellow crystals. yield 77%.

melting point: 272° C. (decomposition). Anal Calcd for C$_8$H$_5$N$_2$S$_2$Na.0.75H$_2$O: C 41.82, H 2.85, N 12.19. Found: C 41.78, H 2.98, N 12.11. ¹H-NMR(DMSO-d$_6$)δ: 7.35 (1H,s), 7.71 (2H,d,J=6.2 Hz), 8.48 (2H,d,J=6.2 Hz).

Reference Example 6

4-(4-pyridyl)-1,3-thiazole-2-thiol sodium salt 4-(4-Pyridyl)-1,3-thiazole-2-thiol (194 g, 1.0 mol) was suspended in methanol (1 L) and a powder of sodium methylate (71.5 g, 1.2 mol) was added at 25° C. The mixture was stirred for 30 min and the reaction mixture was concentrated under reduced pressure to 50-60 mL. The mixture was preserved overnight in a refrigerator. The precipitated crystals were collected by filtration and dried in vacuo in the presence of phosphorus pentoxide at 40° C. to give the title compound (160 g, 0.74 mol). yield: 74%.

Reference Example 7 benzhydryl 7β-[(phenylacetyl)amino]-3-[(methylsulfonyl)oxy]-3-cephem-4-carboxylate Benzhydryl 7β-[(phenylacetyl)amino]-3-hydroxy-3-cephem-4-carboxylate (500 g, 1 mol) was dissolved in acetonitrile (2 L) and ethyldiisopropylamine (183 mL, 1.05 mol) was added dropwise over 10 min with stirring at −40° C. Then, methanesulfonyl chloride (86 mL, 1.1 mol) was added dropwise over 10 min and the mixture was stirred at −40° C. for 40 min. The reaction mixture was poured into iced water (8 L) and the precipitate was collected by filtration. The precipitate was washed with water (2L) and ethyl acetate (300 mL) and dried under reduced pressure to give the title compound (544 g, 0.94 mol) as pale-yellow crystals. yield: 94%.

melting point: 157° C. Anal Calcd for C$_{29}$H$_{26}$N$_2$O$_7$S$_2$: C 60.19, H 4.53, N 4.84; S 11.08. Found: C 59.86, H 4.72, N 4.73, S, 10.77. ¹H-NMR(CDCl$_3$)δ:2.79 (3H,s), 3.48-3.75 (4H,m), 5.02 (1H,d,J=5.2 Hz), 5.90 (1H,dd,J=5.2 Hz,8.8 Hz), 6.24 (1H,d,J=8.8 Hz), 6.93 (1H,s), 7.24-7.41 (15H,m)

Reference Example 8 benzhydryl 7β-[(phenylacetyl)amino]-3-[(methylsulfonyl)oxy]-3-cephem-4-carboxylate Benzhydryl 7β-[(phenylacetyl)amino]-3-hydroxy-3-cephem-4-carboxylate (500 g, 1 mol) was dissolved in acetone (2 L) and methanesulfonyl chloride (86 mL, 1.1 mol) was added dropwise over 10 min with stirring at −20° C. Then, ethyldiisopropylamine (183 mL, 1.05 mol) was added dropwise over 30 min and the mixture was stirred at −20° C. for 40 min. The reaction mixture was poured into iced water (8 L) and the precipitate was collected by filtration. The precipitate was then washed with water (2 L) and ethyl acetate (300 mL), and dried under reduced pressure to give the title compound (523 g, 0.90 mol). yield: 90%.

Reference Example 9 benzhydryl 7β-[(phenylacetyl)amino]-3-[4-pyridyl-2-thiazolylthio]-3-cephem-4-carboxylate 4-(4-Pyridyl)-1,3-thiazole-2-thiol sodium salt (194 g, 1 mol) prepared according to the method of Reference Example 5 was suspended in tetrahydrofuran (1.5 L) and benzhydryl 7β-[(phenylacetyl)amino]-3-[(methylsulfonyl)oxy]-3-cephem-4-carboxylate (196 g, 0.91 mol) dissolved in tetrahydrofuran (3.0 L) was added dropwise under ice-cooling over 30 min. The mixture was stirred at 0° C. for 2 hr and saturated brine (7 L) was added. The mixture was extracted with ethyl acetate (5 L). The organic layer was washed with saturated brine (5 L) and dried over anhydrous sodium sulfate. The solvent was concentrated under reduced pressure to give the title compound as crystals. The crystals were suspended in ethyl acetate (0.5 L), collected by filtration on a glass filter and washed with methanol (1 L×2). The crystals were dried in vacuo to give the title compound (412 g, 0.71 mol). yield: 78%. melting point: 134° C. Anal Calcd for C$_{36}$H$_{28}$N$_4$O$_4$S$_3$.0.5H$_2$O: C 63.05, H 4.11, N 8.17, S 14.02. Found: C 63.16, H 4.15, N 8.27, S 13.98. ¹H-NMR(CDCl$_3$) δ:3.41-3.73 (4H,m), 5.02 (1H,d,J=4.8 Hz), 5.84 (1H,dd,J=4.8 Hz,8.8 Hz), 6.23 (1H,d,J=8.8 Hz), 6.97 (1H,s), 7.27-7.72 (17H,m), 7.73 (1H,s), 8.67 (1H,d,J=6.2 Hz).

Reference Example 10 benzhydryl 7β-[(phenylacetyl)amino]-3-[4-pyridyl-2-thiazolylthio]-3-cephem-4-carboxylate 4-(4-Pyridyl)-1,3-thiazole-2-thiol (225 g, 1.16 mol) was suspended in tetrahydrofuran (1.5 L) and 28% sodium methylate-methanol solution (235 g, 1.22 mol) was added dropwise at 25° C. over 10 min. The mixture was stirred for 1 hr. The reaction mixture was ice-cooled and benzhydryl 7β-[(phenylacetyl)amino]-3-[(methylsulfonyl)oxy]-3-cephem-4-carboxylate (479 g, 0.83 mol) dissolved in tetrahydrofuran (3.5 L) was added dropwise over 30 min. The mixture was stirred at 0° C. for 1 hr and a mixture of acetic acid (50 mL), methanol (5 L) and water (7 L) was added dropwise over 30 min. The mixture was stirred at 0° C. for 2 hr, and the precipitated crystals were collected by filtration. The obtained crystals were washed with methanol (1 L×2) and dried in vacuo to give the title compound (438 g, 0.63 mol). yield: 76%.

Reference Example 11 benzhydryl 7β-[(phenylacetyl)amino]-3-[4-(1-methyl-4-pyridinio)-2-thiazolylthio]-3-cephem-4-carboxylate iodide Benzhydryl 7β-[(phenylacetyl)amino]-3-[4-pyridyl-2-thiazolylthio]-3-cephem-4-carboxylate (300 g, 0.43 mol) was dissolved in tetrahydrofuran (0.6 L) and methyl iodide (324 g, 2.17 mol) was added at 25° C. After stirring for 8 hr, the reaction mixture was poured into ethyl acetate (6 L). The precipitate was collected by filtration. The obtained precipitate was washed with ethyl acetate (0.5 L) and diethyl ether (1 L), and dried in vacuo to give the title compound (351 g, 0.42 mol) as a yellow powder. yield: 97%.
$^1$H-NMR(CDCl$_3$)δ:3.58 (2H,dd,J=4.8 Hz,6.6 Hz), 3.74 (2H,brs), 4.35 (3H,s), 5.11 (1H,d,J=4.8 Hz), 5.89 (1H,d,J=4.8 Hz), 6.95 (1H,s), 7.18-7.42 (15H,m), 8.30 (2H,d,J=6.6 Hz), 8.41 (1H,s), 8.75 (2H,d,J=6.6 Hz).

Reference Example 12 benzhydryl 7β-[(phenylacetyl)amino]-3-[4-(1-methyl-4-pyridinio)-2-thiazolylthio]-3-cephem-4-carboxylate iodide Benzhydryl 7β-[(phenylacetyl)amino]-3-[4-pyridyl-2-thiazolylthio]-3-cephem-4-carboxylate (300 g, 0.43 mol) was dissolved in N,N-dimethylformamide (0.6 L), and methyl iodide (648 g, 4.34 mol) was added at 25° C. After stirring for 16 hr, the reaction mixture was poured into ethyl acetate (6 L), and the precipitate was collected by filtration. The precipitate was washed with ethyl acetate (0.5 L) and diethyl ether (1 L), and dried in vacuo to give the title compound (317 g, 0.39 mol) as a yellow powder. yield: 89%.

Reference Example 13 benzhydryl 7β-amino-3-[4-(1-methyl-4-pyridinio)-2-thiazolylthio]-3-cephem-4-carboxylate chloride monohydrochloride Phosphorus pentachloride (312 g, 1.44 mol) was suspended in dichloromethane (2.8 L), and pyridine (115 g, 1.44 mol) was added dropwise under ice-cooling over 10 min. The mixture was stirred for 30 min. Then, a powder (400 g, 0.48 mol) of benzhydryl 7β-[(phenylacetyl)amino]-3-[4-(1-methyl-4-pyridinio)-2-thiazolylthio]-3-cephem-4-carboxylate iodide was added over 10 min and the mixture was stirred for 1 hr. The reaction mixture was cooled to −10° C. and isobutyl alcohol (5.6 L) was added. The mixture was stirred at 25° C. for 3 hr. Then ethyl acetate (6 L) was added and the mixture was further stirred for 3 hr. The precipitate was collected by filtration on a glass filter, washed with ethyl acetate (0.5 L) and diethyl ether (1 L), and dried in vacuo to give the title compound (270 g, 0.42 mol) as a pale-yellow powder. yield: 87%.
$^1$H-NMR(DMSO-d$_6$)δ:3.94 (2H,brs), 4.35 (3H,s), 5.32 (1H,d,J=5.0 Hz), 5.45 (1H,d,J=5.0 Hz), 6.99 (1H,s), 7.25-7.40 (10H,m), 8.59 (2H,d,J=7.0 Hz), 9.07 (2H,d,J=7.0 Hz), 9.19 (1H,s).

Reference Example 14

7β-amino-3-[4-(1-methyl-4-pyridinio)-2-thiazolylthio]-3-cephem-4-carboxylate dihydrochloride Benzhydryl 7β-amino-3-[4-(1-methyl-4-pyridinio)-2-thiazolylthio]-3-cephem-4-carboxylate chloride monohydrochloride (430 g, 0.66 mol) was suspended in acetonitrile (3.5 L) and conc. hydrochloric acid (3.5 L) was added. The mixture was stirred for 10 min. Then, ethyl acetate (7 L) was added to the reaction mixture, and the mixture was stirred for 5 hr. The precipitate was collected by filtration, washed with acetonitrile (1L×2), and dried in vacuo to give the title compound (236 g, 0.49 mol) as pale-yellow crystals. yield: 74%.
melting point: 202° C. (decomposition) Anal Calcd for $C_{16}H_{14}N_4O_3S_3$·2HCl: C 40.08, H 3.36, N 11.69, S 20.07. Found: C 39.83, H 3.43, N 11.78, S 20.03. $^1$H-NMR(DMSO-d$_6$)δ:3.90 (2H,dd,J=17.2 Hz,17.6 Hz), 4.35 (3H,s), 5.26 (1H,d,J=5.0 Hz), 5.42 (1H,d,J=5.0 Hz), 8.61 (2H,d,J=7.0 Hz), 9.05 (2H,d,J=7.0 Hz), 9.17 (1H,s).

Reference Example 15

7β-amino-3-[4-(1-methyl-4-pyridinio)-2-thiazolylthio]-3-cephem-4-carboxylate dihydrochloride Phosphorus pentachloride (31.2 g, 144 mmol) was suspended in dichloromethane (250 mL) and pyridine (11.5 g, 144 mmol) was added dropwise under ice-cooling over 10 min. The mixture was stirred for 30 min. Then, a powder (41.7 g, 48 mmol) of benzhydryl 7β-[(phenylacetyl)amino]-3-[4-(1-methyl-4-pyridinio)-2-thiazolylthio]-3-cephem-4-carboxylate iodide was added over 10 min, and the mixture was stirred for 1 hr. The reaction mixture was cooled to −10° C. and isobutyl alcohol (250 mL) was added. The mixture was stirred at 25° C. for 3 hr. The reaction mixture was concentrated to about 100 mL and acetonitrile (250 mL) and then conc. hydrochloric acid (250 mL) were added. The mixture was stirred at 40° C. for 2 hr. The precipitate was collected by filtration, washed with acetonitrile (100 mL×2), and dried in vacuo to give the title compound (14.5 g, 0.30 mol). yield: 63%.

Reference Example 16

7β-amino-3-[4-(1-methyl-4-pyridinio)-2-thiazolylthio]-3-cephem-4-carboxylate monohydrochloride Lyophilized product (5.8 g, 14.3 mmol) of 7β-amino-3-[4-(1-methyl-4-pyridinio)-2-thiazolylthio]-3-cephem-4-carboxylate was dissolved in water (290 mL) and 1N hydrochloric acid was added under ice-cooling to adjust pH to 1.3. The solution was concentrated to about 30 mL under reduced pressure, and ethanol (70 mL) was gradually added under ice-cooling with shaking. The mixture was stood under ice-cooling for 2 hr. The precipitated crystals were collected by filtration, washed with ethanol/water (5:1, 30 mL) and dried under reduced pressure. yield: 4.1 g (65%)
melting point: 120-140° C. (decomposition) Anal Calcd for $C_{16}H_{15}N_4O_3S_3Cl\cdot3.0H_2O$: C, 38.67; H, 4.26; N, 11.27; Cl, 8.00. Found: C, 38.58; H, 3.92; N, 11.26; Cl, 8.18. $^1$H-NMR (D$_2$O) δ: 3.64, 3.99 (2H,ABq,J=18 Hz), 4.37 (3H, s), 5.23 (1H,d,J=5 Hz), 5.44 (1H,d,J=5 Hz), 8.31, 8.76 (each 2H,d,J=7 Hz), 8.51(1H,s). IR (KBr) cm$^{-1}$: 3400, 1800, 1770, 1640, 1530, 1405, 1330, 1190, 1020.

Reference Example 17

2-(5-dichlorophosphorylamino-1,2,4-thiadiazol-3-yl)-2(Z)-ethoxyiminoacetyl chloride Phosphorus pentachloride (1.46 g, 7.0 mmol) was suspended in ethyl acetate (4.17 mL) and the mixture was stirred under ice-cooling for 5 min. 2-(5-Amino-1,2,4-thiadiazol-3-yl)-2(Z)-ethoxyiminoacetic acid (600 mg, 2.77 mmol) was added at once with stirring under ice-cooling for dissolution. The mixture was stirred under ice-cooling for 30 min. The reaction mixture was diluted with toluene (16.8 mL) under ice-cooling for dissolution. To this solution was added saturated brine (11.1 mL) cooled to not higher than −5° C., and the mixture was stirred under ice-cooling for 5 min. The reaction mixture was transferred to a separating funnel and the organic layer was separately taken without shaking. The organic layer was dried over magnesium sulfate. After filtration, the mother liquor was evaporated off under reduced pressure and the residue was stood under ice-cooling for 30 min (crystals precipitated from the residual oil). Diisopropyl ether/n-hexane (1:1, 5.67 mL) was added and the crystals were pulverized with a spatula. The mixture was stood under ice-cooling for 15 min. The precipitated crystals were collected by filtration, washed with diisopropyl ether/n-hexane (1:1, 5.67 mL) and dried under reduced pressure. yield: 631 mg (64%)

melting point: 116-119° C. Anal Calcd for $C_6H_6N_4O_3SCl_3P$: C 20.50, H 1.72, N 15.94, P 8.81. Found: C 20.52, H 1.77, N 15.99, P 8.90. $^1$H-NMR (CDCl$_3$) δ: 1.42 (3H,t,J=7 Hz), 4.45 (2H,q,J=7 Hz), 8.81 (1H,br s). IR (KBr) cm$^{-1}$: 3063, 2984, 1784, 1593, 1223, 1057.

Reference Example 18

2-(5-dichlorophosphorylamino-1,2,4-thiadiazol-3-yl)-2(Z)-ethoxyiminoacetyl chloride Phosphorus pentachloride (78 g, 375 mmol) was suspended in ethyl acetate (225 mL) and 2-(5-amino-1,2,4-thiadiazol-3-yl)-2(Z)-ethoxyiminoacetic acid (32.4 g, 150 mmol) was added with stirring under ice-cooling. The mixture was stirred under ice-cooling for 30 min. The reaction mixture was diluted with toluene (900 mL) under ice-cooling for dissolution. To this solution was added saturated brine (600 mL) cooled to not higher than −5° C., and the mixture was stirred under ice-cooling for 10 min. The reaction mixture was transferred to a separating funnel and the organic layer was separately taken. The organic layer was dried over magnesium sulfate. After filtration, the mother liquor was evaporated off under reduced pressure (crystals precipitated). Diisopropyl ether (300 mL) was added and the crystals were pulverized with a spatula. The mixture was stirred under ice-cooling for 30 min and stood for 30 min. The precipitated crystals were collected by filtration, washed with diisopropyl ether (20 mL) and dried under reduced pressure. yield: 23.5 g (45%)

melting point: 116-119° C. Anal Calcd for $C_6H_6N_4O_3SCl_3P$: C 20.50, H 1.72, N 15.94, P 8.81. Found: C 20.52, H 1.77, N 15.99, P 8.90. $^1$H-NMR (CDCl$_3$) δ: 1.42 (3H,t,J=7 Hz), 4.45 (2H,q,J=7 Hz), 8.81 (1H,br s). IR (KBr) cm$^{-1}$: 3063, 2984, 1784, 1593, 1223, 1057.

Reference Example 19

2-(5-dichlorophosphorylamino-1,2,4-thiadiazol-3-yl)-2(Z)-ethoxyiminoacetyl chloride 2-(5-Amino-1,2,4-thiadiazol-3-yl)-2(Z)-ethoxyiminoacetic acid (1.0 kg, 4.6 mol) was suspended in ethyl acetate (2.4 L) and diisopropyl ether (1.6 L), and cooled to not higher than −1° C. with nitrogen gas substitution. Phosphorus pentachloride (2.0 kg, 9.6 mol) was added at not higher than 5° C. and the mixture was stirred for 30 min. Diisopropyl ether (2.0 L), water (120 mL) and n-hexane (12 L) were added at not higher than 2° C. and the mixture was stirred at the same temperature for 1 hr. The precipitated crystals were collected by filtration under a nitrogen stream, washed with diisopropyl ether/n-hexane (1:2, 2.0 L) and n-hexane (2.0 L) and dried by through-flow under a nitrogen stream. yield: 876.0 g (49.7%)

Reference Example 20

3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate Disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate (1.43 g, 1.96 mmol) was gradually dissolved in 1% (v/v) aqueous acetic acid (14 mL) at room temperature. The solution was filled in an SP-207 column (60 mL). After successive elution with 2%(w/v) brine (180 mL) and 3% (v/v) aqueous ethanol (60 mL), a fraction (1500 mL) containing the title compound eluted with 10% (v/v) aqueous ethanol was collected and concentrated to about 20 mL under reduced pressure. 6N Hydrochloric acid (about 1.5 mL) was gradually added with shaking under ice-cooling to adjust to pH 0.5. A white powder was precipitated. This was stood under ice-cooling for 30 min and the precipitated powder was collected by filtration and washed 3 times with distilled water (2 mL). Using molecular sieves 3A (1/16) as a drying agent, the powder was dried under reduced pressure to a constant weight. yield: 800 mg (59%)

Anal Calcd for $C_{22}H_{21}N_8O_8S_4P\cdot2.0H_2O$: C 36.66, H 3.50, N 15.55, P 4.30. Found: C 36.94, H 3.46, N 15.57, P 3.95. $^1$H-NMR (DMSO-d$_6$) δ: 1.23 (3H,t,J=7 Hz), 3.58, 3.94 (2H, ABq,J=18 Hz), 4.17 (2H,q,J=7 Hz), 4.33 (3H,s), 5.32 (1H,d, J=5 Hz), 5.90 (1H,dd,J=5&8 Hz), 8.51 (2H,d,J=6 Hz), 8.99 (3H,m), 9.30 (1H,m), 9.70 (1H,d,J=8 Hz). IR (KBr) cm$^{-1}$: 3055, 1778, 1682, 1643, 1520, 1385, 1190, 1038.

Reference Example 21

3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate Disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate (128 g, 1.96 mmol) was gradually dissolved in 1% (v/v) aqueous acetic acid (1.28 L) at room temperature. The solution was filled in an SP-207 column (2.5 L). After elution with 1% (v/v) aqueous acetic acid (9 L), a fraction (32 L) containing the title compound eluted with 0.1M sodium acetate:0.1M acetic acid:ethanol (960:30:110) was collected and concentrated to about 700 mL under reduced pressure. 6N Hydrochloric acid (480 mL) was gradually added with shaking under ice-cooling to adjust pH to 0.5. A white powder was precipitated. This was stood under ice-cooling for 30 min and the precipitated powder was collected by filtration and washed with distilled water (300 mL). Using molecular sieves 3A (1/16) as a drying agent, the powder was dried under reduced pressure to a constant weight. yield: 60.9 g (68%)

Anal Calcd for $C_{22}H_{21}N_8O_8S_4P \cdot 2.0H_2O$: C 36.66, H 3.50, N 15.55, P 4.30. Found: C 36.94, H 3.46, N 15.57, P 3.95. $^1$H-NMR (DMSO-$d_6$) δ: 1.23 (3H,t,J=7 Hz), 3.58, 3.94 (2H, ABq,J=18 Hz), 4.17 (2H,q,J=7 Hz), 4.33 (3H,s), 5.32 (1H,d, J=5 Hz), 5.90 (1H,dd,J=5&8 Hz), 8.51 (2H,d,J=6 Hz), 8.99 (3H,m), 9.30 (1H,m), 9.70 (1H,d,J=8 Hz). IR (KBr) cm$^{-1}$: 3055, 1778, 1682, 1643, 1520, 1385, 1190, 1038.

Reference Example 22 disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate 7β-Amino-3-[4-(1-methyl-4-pyridinio)-2-thiazolylthio]-3-cephem-4-carboxylate 1.30 kg (2.71 mol) was suspended in water (7.80 L) and 3M sodium acetate (1.81 L, 5.42 mol) and triethylamine (2.0 L, 14.4 mol) were successively added under ice-cooling. 2-(5-Dichlorophosphorylamino-1,2,4-thiadiazol-3-yl)-2(Z)-ethoxyiminoacetyl chloride (1143.7 g, 3.25 mol) was dissolved in tetrahydrofuran (3.1 L) and the solution was cooled to not higher than −20° C. and added to the above-mentioned reaction mixture. The temperature of the mixture was raised to 15-25° C., and 3M sodium acetate (5.78 L, 17.4 mol) and ethyl acetate (6.50 L) were successively added for partitioning. Ethanol (30 L) was added dropwise to the aqueous layer, and after ice-cooling, the precipitated powder was collected by filtration and washed successively with water/ethanol (1:2, 6.5 L) and ethanol (13 L). After through-flow drying, the powder was dissolved in diluted brine (19.5 L) and the solution was used as a stock solution for column chromatography. yield: 23.3 kg (content 6.61%, yield: 78%)

Reference Example 23 disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate 7β-Amino-3-[4-(1-methyl-4-pyridinio)-2-thiazolylthio]-3-cephem-4-carboxylate (5.0 g, 10.41 mmol) was suspended in water/tetrahydrofuran (5:1, 30 mL) and 3M sodium acetate (6.9 mL, 20.8 mmol) was added dropwise. Triethylamine (7.2 mL, 52.0 mmol) was added under ice-cooling. 2-(5-Dichlorophosphorylamino-1,2,4-thiadiazol-3-yl)-2(Z)-ethoxyiminoacetyl chloride (5.87 g, 16.7 mmol) was dissolved in tetrahydrofuran (12 mL) and added dropwise to the above-mentioned reaction mixture. The temperature of the mixture was raised to 15-30° C., and 3M sodium acetate (28.4 mL, 85.3 mmol) and ethyl acetate (25 mL) were successively added for partitioning. Ethanol (120 mL) was added dropwise to the aqueous layer, and after ice-cooling, the precipitated powder was collected by filtration, washed successively with water/ethanol (1:2) and ethanol, and dried by through-flow. yield: 7.78 g (content 66.2%, yield: 70%)

Reference Example 24 disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate 7β-Amino-3-[4-(1-methyl-4-pyridinio)-2-thiazolylthio]-3-cephem-4-carboxylate (5.00 g, 10.4 mmol) was suspended in water/acetonitrile (10:1, 33 mL) and a part of triethylamine (19.1 mL, 70.7 mmol) was added under ice-cooling. 2-(5-Dichlorophosphorylamino-1,2,4-thiadiazol-3-yl)-2(Z)-ethoxyiminoacetyl chloride (5.87 g, 16.6 mmol) was dissolved in acetonitrile (12 mL) and added dropwise to the above-mentioned reaction mixture while the remainder of triethylamine was added dropwise. The temperature of the mixture was raised to 25° C., and 3M sodium acetate (19.1 mL, 57.2 mmol) and ethyl acetate (25 mL) were successively added for partitioning. Ethanol (120 mL) was added dropwise to the aqueous layer, and after ice-cooling, the precipitated powder was collected by filtration. The powder was washed successively with water/ethanol (1:2, 25 mL) and ethanol (50 mL), and dried by through-flow. yield: 6.78 g (content 73.1%, yield: 68%)

Reference Example 25

Purification of disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate An aqueous solution (7.33 kg, content 4.98%, 0.516 mol) of disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate was applied to SP-207 column chromatography (18 L) and successively eluted with diluted brine and aqueous ethanol. The resulting mainly eluted solution was concentrated by evaporator. recovery: 2.16 kg (content 14.4%, yield: 83%)

Reference Example 26

3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate Activated carbon (15.3 g) was added to an aqueous solution (1.89 kg, content 16.1%, 0.419 mol) of disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate and the mixture was stirred. After filtering off the activated carbon, the residue was washed with water. Water was added to the filtrate to 3.96 kg. Acetic acid (95.0 mL, 1.68 mol) was added and ethanol (4 L) was added. 6N Hydrochloric acid (154 mL, 0.922 mol) was added and the mixture was ice-cooled. The precipitated powder was collected by filtration. The powder was successively washed with water/ethanol (1.0:1.1, 0.71 L) and ethanol (2.1 L) and dried by through-flow. yield: 249.7 g (content 90.8%, yield: 80%)

Reference Example 27

3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate Water was added to an aqueous solution (57.3 g, content 8.73%, 6.86 mmol) of disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate to 65 g. Acetic acid (1.57 mL, 26.2 mmol) and ethanol (65 mL) were added at room temperature and 10% sulfuric acid (8.7 mL, 8.88 mmol) was added dropwise. After stirring under ice-cooling, the precipitated powder was collected by filtration. The powder was successively washed with water/ethanol (1:1, 10 mL) and ethanol (30 mL) and dried in vacuo. yield: 3.8 g (81%)

Reference Example 28

3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate Water was added to an aqueous solution (664 g, content 12.1%, 0.114 mol) of disodium 3-[4-(1-methyl-4-pyridinio)-2-thiazolylthio]-7β-[2-(5-phosphonateamino-1,2,4-thiadiazol-3-yl)-2(Z)-ethoxyiminoacetamido]-3-cephem-4-carboxylate to 1044 g. 6N Hydrochloric acid (56.9 mL, 0.341 mol) was added dropwise at not higher than 10° C., and after stirring, the precipitated powder was collected by filtration. The powder was washed with water (563 mL) and dried in vacuo. yield: 81.4 g (content 81.6%, yield 81%)

Reference Example 29

4-(4-pyridyl)-1,3-thiazole-2-thiol 4-(4-Pyridyl)-1,3-thiazole-2-thiol.hydrobromide (89.3 g, 0.32 mol) was suspended in water (627 mL) under a nitrogen stream, and 25% aqueous sodium hydroxide solution (110.5 g, 0.69 mol) was added for dissolution. An insoluble material was filtered and washed with water (100 mL). 35% Hydrochloric acid (31 mL) was added to the filtrate to adjust to pH 6.8. The precipitated crystals were collected by filtration, and washed with water (20 mL) and methanol (20 mL). The obtained crystals were suspended in methanol (627 mL). After stirring for 2 hr, the crystals were filtrated and dried. yield: 47.6 g (75.6%)

Reference Example 30 benzhydryl 7β-[(phenylacetyl)amino]-3-[4-(4-pyridyl)-2-thiazolylthio]-3-cephem-4-carboxylate Benzhydryl 7β-[(phenylacetyl)amino]-3-[(methylsulfonyl)oxy]-3-cephem-4-carboxylate (900 g, 1.56 mol) was dissolved in tetrahydrofuran (3.6 L) and cooled to −3° C. While maintaining the same temperature, 28% sodium methylate-methanol solution (360 g, 1.87 mol) of 4-(4-pyridyl)-1,3-thiazole-2-thiol (362.5 g, 1.87 mol) obtained in the same manner as in Reference Example 29, and tetrahydrofuran (720 mL) solution were added. The mixture was stirred for 1.5 hr. Acetic acid (18.7 g) was added and after stirring for 30 min, methanol (9 L) and water (5.4 L) were added. The mixture was stirred for 2 hr. The precipitated crystals were collected by filtration, washed with methanol (16 L) and dried in vacuo. yield: 884 g (84%)

Experimental Example 1

The crystals (102.4 mg, 0.131 mmol) of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with acetic acid, and sodium hydrogencarbonate (27.6 mg, 0.328 mmol) were filled in a vial, and then a physiological saline solution (0.918 mL) was gradually added. These compounds dissolved while generating carbon dioxide gas and gave a clear solution. This solution was diluted with a physiological saline solution to 2.0 mL, whereby a medication solution having a concentration of 50 mg/mL was prepared.

Experimental Example 2

The crystals (101.9 mg, 0.129 mmol) of 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate with propionic acid, and sodium hydrogencarbonate (27.1 mg, 0.322 mmol) were filled in a vial, and then a physiological saline solution (0.902 mL) was gradually added. These compounds dissolved while generating carbon dioxide gas and gave a clear solution. This solution was diluted with a physiological saline solution to 2.0 mL, whereby a medication solution having a concentration of 50 mg/mL was prepared.

Experimental Example 3

3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (250 mg, 0.336 mmol), sodium carbonate (42.7 mg, 0.403 mmol) and sodium hydrosulfite (29.2 mg, 0.168 mmol) were filled in a vial, and then a physiological saline solution (5 mL) was added to give a clear solution.

Experimental Example 4

3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (250 mg, 0.336 mmol), sodium carbonate (42.7 mg, 0.403 mmol) and sodium sulfite (21.2 mg, 0.168 mmol) were filled in a vial, and then a physiological saline solution (5 mL) was added to give a clear solution.

Experimental Example 5

3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (250 mg, 0.336 mmol), sodium carbonate (42.7 mg, 0.403 mmol) and sodium sulfite (0.42 mg, 0.003 mmol) were filled in a vial, and then a physiological saline solution (5 mL) was added to give a clear solution.

Experimental Example 6

3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (250 mg, 0.336 mmol) and sodium carbonate (42.8 mg, 0.403 mmol) were filled in a vial, and then a 5% glucose solution (5 mL) containing sodium sulfite (1.25 mg) was added to give a clear solution.

Experimental Example 7

3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (250 mg, 0.336 mmol) and sodium carbonate (42.8 mg, 0.403 mmol) were filled in a vial, and then a 5% glucose solution (5 mL) containing sodium hydrogen sulfite (1.25 mg) was added to give a clear solution.

Experimental Example 8

3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (250 mg, 0.336 mmol) and sodium carbonate (42.8 mg, 0.403 mmol) were filled in a vial, and then a 5% glucose solution (5 mL) containing sodium pyrosulfite (1.25 mg) was added to give a clear solution.

Experimental Example 9

3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (250 mg, 0.336 mmol) and sodium carbonate (42.8 mg, 0.403 mmol) were filled in a vial, and than a 5% glucose solution (5 mL) containing L-cysteine (1.25 mg) was added to give a clear solution.

Experimental Example 10

3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (567 mg, 0.76 mmol), L-arginine (381.6 mg, 2.19 mmol) and sodium sulfite (4.6 mg, 0.036 mmol) were filled in a vial, and then a physiological saline solution (50 mL) was added to give a clear solution.

Experimental Example 11

3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (567 mg, 0.76 mmol), L-arginine (381.6 mg, 2.19 mmol) and sodium sulfite (18.4 mg, 0.15 mmol) were filled in a vial, and then a physiological saline solution (50 mL) was added to give a clear solution.

Experimental Example 12

L-Arginine (81.4 mg, 3.2 equivalents) and sodium sulfite (1.8 mg, 0.1 equivalent) were added to 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (113.4 mg), and filled in a 13P vial. The space was substituted by low humidity air to give a pharmaceutical preparation.

The obtained formulation was dissolved in a physiological saline solution (2 mL), which remained clear for 24 hr.

The obtained pharmaceutical preparation was subjected to a stability test. The formulation was stable as shown by the results in Table 1.

TABLE 1

| Preservation conditions | Remaining ratio | Dissolution state* |
|---|---|---|
| 60° C. × 2 weeks | 97.7% | clear |
| 60° C. × 4 weeks | 96.4% | clear |
| 40° C./75% RH × 1 month | 99.6% | clear |
| 40° C./75% RH × 2 months | 95.8% | clear |
| 25° C. × 1 month | 100.4% | clear |
| 25° C. × 2 months | 98.0% | clear |

RH: relative humidity
*Dissolution state for 24 hr after dissolution in a physiological saline solution (2 mL).

Experimental Example 13

L-Arginine (763.3 mg, 3.0 equivalents) and sodium sulfite (18.4 mg, 0.1 equivalent) were added to 3-[4-(1-methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (1.135 g) and filled in a 35K vial. The space was substituted by low humidity air to give a pharmaceutical preparation.

The obtained formulation was dissolved in a physiological saline solution (10 mL), which remained clear for 24 hr.

Experimental Example 14

3-[4-(1-Methyl-4-pyridinio)-2-thiazolylthio]-7β-[2-(5-phosphonoamino-1,2,4-thiadiazol-3-yl)-2(Z)-ethoxyiminoacetamido]-3-cephem-4-carboxylate.acetic acid solvate (1.135 g) was filled in a 35K vial. The space was substituted by low humidity air and sealed with a rubber cap to give a pharmaceutical preparation.

As sole use solvent, L-arginine (763.3 mg, 3.0 equivalents) and sodium sulfite (18.4 mg, 0.1 equivalent) were dissolved in 10 mL of distilled water and filled in an ampoule (10P). The space was substituted by nitrogen and the ampoule was melt-sealed.

The above-mentioned formulation was dissolved with the sole use solvent. The solution remained clear for 24 hr after dissolution, showing the same level of quality of injection as in Example 14.

The L-arginine content and sodium sulfite content after autoclaving the sole use solvent at 121° C.×20 min were measured by potentiometer and ion chromatography, respectively. As shown in Table 2, the sole use solvent did not show degradation in quality even after autoclaving.

TABLE 2

| Autoclave treatment | L-Arginine | Sodium sulfite content | Dissolution state |
|---|---|---|---|
| applied | 100.2% | 99.8% | clear |
| none | 99.0% | 99.0% | clear |

INDUSTRIAL APPLICABILITY

The compound (particularly crystal) of the present invention shows high solid stability and can be used as an antibacterial agent (particularly anti-MRSA agent) having superior quality, such as possible long-term stable preservation and the like.

This application is based on patent application Nos. 247966/2000 and 354959/2000 filed in Japan, the contents of which are hereby incorporated by reference.

What is claimed is:

1. A pharmaceutical composition comprising a pH adjuster and a compound of formula (I):

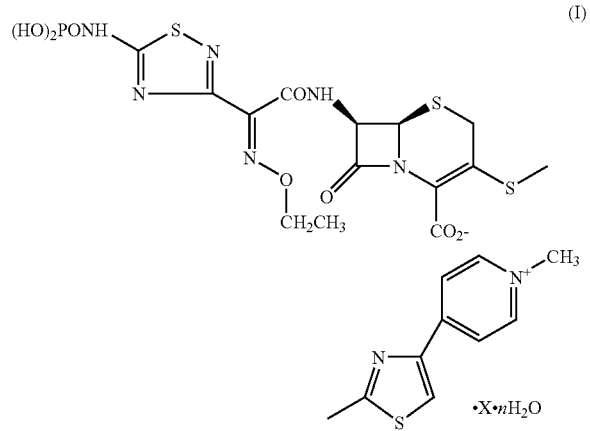

wherein X is $CH_3COOH$ or $CH_3CH_2COOH$ and n is 0-5.

2. The composition of claim 1 wherein the compound of formula (I) is in the form of a crystal.

3. The composition of claim 1 wherein n is 1.

4. The composition of claim 1 wherein X is $CH_3COOH$.

5. The composition of claim 4 wherein the compound of formula (I) has peaks near diffraction angles of 16.32, 19.06, 19.90, 20.98 and 23.24° in powder X-ray diffraction (CuKα).

6. The composition of claim 4 wherein the compound of formula (I) has peaks near diffraction angles of 11.82, 17.16, 17.80, 19.32, 20.00, 21.20, 21.78, 22.94, 24.10 and 27.02° in powder X-ray diffraction (CuKα).

7. The composition of claim 1, wherein X is $CH_3COOH$ and n is 1.

8. The composition of claim 1 wherein the pH adjuster is a basic amino acid or a carbonate of an alkaline metal or alkaline earth metal.

9. The composition of claim 1 wherein the pH adjuster is L-arginine.

10. The composition of claim 1 wherein the pH adjuster is present in an amount sufficient to make the pH of a solution of the composition in the range of pH 4 to pH 10.

11. The composition of claim 1 wherein the pH adjuster is present in an amount sufficient to make the pH of a solution of the composition in the range of pH 4.5 to pH 8.5.

12. The composition of claim 1 wherein the pH adjuster is present in an amount sufficient to make the pH of a solution of the composition in the range of pH 5.0 to pH 8.0.

13. The composition of claim 1 wherein the pH adjuster is present in an amount sufficient to make the pH of a solution of the composition in the range of pH 5.0 to pH 7.5.

14. The composition of claim 9 wherein the L-arginine is present in an amount ranging from 0.1 to 5.0 equivalents relative to the amount of the compound of formula (I).

15. The composition of claim 9 wherein the L-arginine is present in an amount ranging from 2.0 to 3.5 equivalents relative to the amount of the compound of formula (I).

16. The composition of claim 9 wherein the L-arginine is present in an amount ranging from 2.5 to 3.2 equivalents relative to the amount of the compound of formula (I).

17. The composition of claim 1 further comprising a solubilizing agent selected from the group consisting of sodium sulfite, sodium hydrosulfite, sodium hydrogen sulfite, sodium pyrosulfite and L-cysteine.

18. The composition of claim 17 wherein the solubilizing agent is present in an amount ranging from 0.001 to 2.0 equivalents relative to the amount of the compound of formula (I).

19. The composition of claim 17 wherein the solubilizing agent is present in an amount ranging from 0.01 to 0.5 equivalents relative to the amount of the compound of formula (I).

20. The composition of claim 17 wherein the solubilizing agent is present in an amount ranging from 0.05 to 0.2 equivalents relative to the amount of the compound of formula (I).

21. The composition of claim 1, further comprising a solvent.

22. The composition of claim 21, wherein the solvent is water, physiological saline or a 5% glucose solution.

23. The composition of claim 7, wherein the pH adjuster is L-arginine.

* * * * *